United States Patent [19]
An

[11] Patent Number: 5,861,542
[45] Date of Patent: Jan. 19, 1999

[54] GENE CONTROLLING FLORAL DEVELOPMENT AND APICAL DOMINANCE IN PLANTS

[75] Inventor: Gynheung An, Pullman, Wash.

[73] Assignee: Washington State University Research Foundation, Pullman, Wash.

[21] Appl. No.: 485,981

[22] Filed: Jun. 7, 1995

Related U.S. Application Data

[63] Continuation-in-part of Ser. No. 323,449, Oct. 14, 1994.
[51] Int. Cl.$^6$ .............................. A01H 5/00; C12N 5/04; C12N 15/29; C12N 15/82
[52] U.S. Cl. ....................... 800/205; 536/23.6; 435/69.1; 435/70.1; 435/172.3; 435/320.1; 435/419; 47/58
[58] Field of Search ......................... 536/23.6; 435/69.1, 435/70.1, 172.3, 240.4, 320.1, 419; 800/205; 47/58

[56] References Cited

U.S. PATENT DOCUMENTS 5,444,179  8/1995  Izhar et al. ............................. 800/200

OTHER PUBLICATIONS

Schmidt et al. 1993, Plant Cell 5(7):729–737.
Kano–Murakami et al., "A Rice Homeotic Gene, OSH1, Causes Unusual Phenotypes in Transgenic Tobacco," *FEBS Letters* 334:365–368 (1993).
Hansen et al., "NTGLO: A Tobacco Homologue of the GLOBOSA Floral Homeotic Gene of *Antirrhinum majus*: cDNA Sequence and Expression Pattern," *Mol. Gen. Genet.* 239:310–312 (1993).
Matsuoka et al., "Expression of a Rice Homeobox Gene Causes Altered Morphology of Transgenic Plants," *The Plant Cell* 5:1039–1048 (1993).
Coupland, "LEAFY Blooms in Aspen," *Nature* 377:482–483 (1995).
Weigel et al., "A Developmental Switch Sufficient for Flower Initiation in Diverse Plants," *Nature* 377:495–500 (1995).
Mandel et al., "A Gene Triggering Flower Formation in Arabidopsis," *Nature* 377:522–524 (1995).
Ma et al., "AGL1–AGL6, an Arabidopsis Gene Family With Similarity to Floral Homeotic and Transcription Factor Genes," *Genes Dev.* 5:484–495 (1991).
Huijser et al., "Bracteomania, an Inflorescence Anomaly, is Caused by the Loss of Function of the MADS–Box Gene squamosa in Antirrhinum majus," *EMBO J.* 11:1239–1249 (1992).
Schwarz–Sommer et al., "Characterization of the Antirrhinum Floral Homeotic MADS–Box Gene deficiens: Evidence for DNA Binding and Autoregulation of its Persistent Expression Through Fower Development," *EMBO J.* 11:251–263 (1992).
Bradley et al., "Complementary Floral Homeotic Phenotypes Result From Opposite Orientations of a Transposon at the plena Locus of Antirrhinum," *Cell* 72:85–95 (1993).

Kempin et al., "Conversion of Perianth into Reproductive Organs by Ectopic Expression of the Tobacco Floral Homeotic Gene NAGI," *Plant Physiol.* 103:1041–1046 (1993).
Sommer et al., "Deficiens, a Homeotic Gene Involved in the Control of Flower Morphogenesis in Antirrhinum majus: The Protein Shows Homology to Transcription Factors, "*EMBO J.* 9:605–613 (1990).
Angenent et al., "Differential Expression of Two MADS Box Genes in Wild–Type and Mutant Petunia Flowers," *Plant Cell* 4:983–993 (1992).
Chung et al., "Early Flowering and Reduced Apical Dominance Result from Ectopic Expression of a Rice MADS Box Gene," *Plant Mol. Biol.* 0:1–9 (1994).
Tsuchimoto et al., "Ectopic Expression of pMADS3 in Transgenic Petunia Phenocopies the Petunia blind Mutant," *Plant Cell* 5:843–853 (1993).
Coen et al.,"floricaula: A Homeotic Gene Required for Flower Development in Antirrhinum majus," *Cell* 63:1311–1322 (1990).
Trobner et al., "GLOBOSA: A Homeotic Gene Which Interacts With Deficiens in the Control of Antirrhinum Floral Organogenesis," *EMBO J.* 11:4693–4704 (1992).
Jack et al., "The Homeotic Gene APETALA3 of *Arabidopsis thaliana* Encodes a MADS Box and is Expressed in Petals and Stamens," *Cell* 68:683–697 (1992).
Tamsas, "Hormonal Regulation of Apical Dominance." In: Davies PJ (ed), Plant Hormones and Their Role in Plant Growth and Development, pp. 393–410. Martinus Nijhoff Pub., Dordrecht, Netherlands (1987).
Schmidt et al., "Identification and Molecular Characterization of ZAG1, the Maize Homolog of the Arabidopsis Florla Homeotic Gene AGAMOUS," *Plant Cell* 5:729–737 (1993).
Pnueli et al., "Isolation of the Tomato AGAMOUS Gene TAG1 and Analysis of its Homeotic Role in Transgenic Plants," *Plant Cell* 6:163–173 (1994).
Weigel et al., "LEAFY Controls Floral Meristem Identity in Arabidopsis," *Cell* 69:843–859 (1992).
Mandel et al., "Molecular Characterization of the Arabidopsis Floral Homeotic Gene APETALA1," *Nature* 360:273–277 (1992).

(List continued on next page.)

*Primary Examiner*—David T. Fox
*Attorney, Agent, or Firm*—Klarquist Sparkman Campbell Leigh & Whinston, LLP

[57] ABSTRACT

The present invention provides compositions and methods for affecting the transition from vegetative to reproductive growth in a wide variety of plants. A MADS-box gene from rice, OsMADS1, has been isolated and sequenced. Expression of OsMADS1 in transgenic plants dramatically alters development, resulting in early flowering plants with reduced apical dominance, causing both long-day and short-day plants to flower under both short-day and long-day conditions. OsMADS1 is a key regulatory factor determining the transition from shoot apex to floral meristem and is a target for action of flower induction signals.

29 Claims, 4 Drawing Sheets

OTHER PUBLICATIONS

Pnueli et al., "The MADS Box Gene Family in Tomato: Temporal Expression During Floral Development, Conserved Secondary Structures and Homology with Homeotic Genes From Antirrhinum and Arabidopsis," *Plant J.* 1:255–266 (1991).

Mandel et al., "Manipulation of Flower Structure in Transgenic Tobacco," *Cell* 71:133–143 (1992).

Gasser, "Molecular Studies on the Differentiation of Floral Organs," *Annu. Rev. Plant Physiol. Plant Mol. Biol.* 42:621–649 (1991).

Yanofsky et al., "The Protein Encoded by the Arabidopsis Homeotic Gene agamous Resembles Transcription Factors," *Nature* 346:35–39 (1990).

An, "Regulatory Genes Controlling Flowering Time or Floral Organ Development," *Plant Mol. Biol.* 25:335–337 (1994).

Coen, "The Role of Homeotic Genes in Flower Development and Evolution," *Annu. Rev. Plant Physiol. Plant Mol. Biol.* 42:241–279 (1991).

Pnueli et al., "The TM5 MADS Box Gene Mediates Organ Differentiation in Three Inner Whorls of Tomato Flowers," *Plant Cell* 6:175–186 (1994).

Mizukami et al., "Ectopic Expression of the Floral Homeotic Gene AGAMOUS in Transgenic Arabidopsis Plants Alters Floral Organ Identitiy," *Cell* 71:119–131 (1992).

```
   1 AAAACTAGCTTGCAAAGGGGATAGAGTAGTAGAGAGAGAGAGAGAGGAGAGGAGGAGGAA

61 GAAGATGGGGAGGGGGAAGGTGGAGCTGAAGCGGATCGAGAACAAGATCAGCCGGCAGGT
         MetGlyArgGlyLysValGluLeuLysArgIleGluAsnLysIleSerArgGlnVa  19
                                                                    MADS
 121 GACGTTCGCCAAGCGCAGGAACGGCCTGCTCAAGAAGGCCTACGAGCTCTCCCTCCTCTG  BOX
       lThrPheAlaLysArgArgAsnGlyLeuLeuLysLysAlaTyrGluLeuSerLeuLeuCy  39

181 CGACGCCGAGGTCGCCCTCATCATCTTCTCCGGCCGCGGCCGCCTCTTCGAGTTCTCCAG
       sAspAlaGluValAlaLeuIleIlePheSerGlyArgGlyArgLeuPheGluPheSerSe  59

241 CTCATCATGCATGTACAAAACCTTGGAGAGGTACCGCAGCTGCAACTACAACTCACAGGA
       rSerSerCysMetTyrLysThrLeuGluArgTyrArgSerCysAsnTyrAsnSerGlnAs  79

301 TGCAGCAGCTCCAGAAAACGAAATTAATTACCAAGAATACCTGAAGCTGAAAACAAGAGT
       pAlaAlaAlaProGluAsnGluIleAsnTyrGlnGluTyrLeuLysLeuLysThrArgVa  99

361 TGAATTTCTTCAAACCACACAGAGAAATATTCTTGGTGAGGATTTGGGCCCACTAAGCAT
       lGluPheLeuGlnThrThrGlnArgAsnIleLeuGlyGluAspLeuGlyProLeuSerMe 119
                                                                    K BOX
 421 GAAGGAGCTGGAGCAGCTTGAGAACCAGATAGAAGTATCCCTCAAACAAATCAGGTCAAG
       tLysGluLeuGluGlnLeuGluAsnGlnIleGluValSerLeuLysGlnIleArgSerAr 139

481 AAAGAACCAAGCACTGCTTGATCAGCTGTTTGATCTGAAGAGCAAGGAGCAACAGCTGCA
       gLysAsnGlnAlaLeuLeuAspGlnLeuPheAspLeuLysSerLysGluGlnGlnLeuGl 159

541 AGATCTCAACAAAGACTTGAGGAAAAAGTTACAGGAAACCAGTGCAGAGAATGTGCTCCA
       nAspLeuAsnLysAspLeuArgLysLysLeuGlnGluThrSerAlaGluAsnValLeuHi 179

601 TATGTCCTGGCAAGATGGTGGTGGGCACAGCGGTTCTAGCACTGTTCTTGCTGATCAGCC
       sMetSerTrpGlnAspGlyGlyGlyHisSerGlySerSerThrValLeuAlaAspGlnPr 199

661 TCATCACCATCAGGGTCTTCTCCACCCTCACCCAGATCAGGGTGACCATTCCCTGCAGAT
       oHisHisHisGlnGlyLeuLeuHisProHisProAspGlnGlyAspHisSerLeuGlnIl 219

721 TGGGTATCATCACCCTCATGCTCACCATCACCAGGCCTACATGGACCATCTGAGCAATGA
       eGlyTyrHisHisProHisAlaHisHisHisGlnAlaTyrMetAspHisLeuSerAsnGl 239

781 AGCAGCAGACATGGTTGCTCATCACCCCAATGAACACATCCCATCCGGCTGGATATGATG
       uAlaAlaAspMetValAlaHisHisProAsnGluHisIleProSerGlyTrpIle***    257

841 TGTGTGTTCAGTTCAGGCTTCAGGCTTCAGAGAAGCCAATGCAAACAGTGTCCTGTAATC

901 CAGTAATTACAGGGCATATGTAATGTAATGTAATGTAATCCCTGATCTATATTTTGCTAA

961 GTACGTGCGTGCTCTCTTACGACCTTCTCCCCCAAACAGTTAATCAGGGGAATAATAATT

1021 TCGTTTGATGCACGTACTGTATGTCTGTATCTGTCACTGTATCGTAGGACCGTCCATGTA

1081 TAACAATTTCCGTTTTGGATGTGGTAACAATTAATTGGCACTTAAATTTATATTTGTGAT

```
GRGKVELKRIENKISRQVTFAKRRNGLLKKAYELSLLCDAEVALIIFSGRGRLFEF   OsMADS1
****R*Q******N******S****A*******H*I*V*********VV**HK*K***Y   Ap1
****Q******N******S****G*******H***V*********V**NK*K***Y     SQUA
****I*I****TTN******C***************V***S*****Y*Y            AG
****I*I****ITN******C***************VV***S****Y*Y            PLE
*G*R*Q******QTN*****YS*******F***H*TV*****R*SI*M**SSNK*H*Y   Ap3
A***IQI*****QTN*****YS*******F****H***V****K*SI*MI*STQK*H*Y  DEF A
```

FIG. 1B

```
  1 CCGGCCGCTGAAAAAATGGGAAGGGGTAGGGTTGAGCTTAAGAGAATAGAGAACAAGATC
                  M  G  R  G  R  V  E  L  K  R  I  E  N  K  I    15
 61 AACAGGCAAGTGACCTTCGCTAAGAGAAGAAATGGACTTTTGAAAAAAGCTTATGAGCTT
    N  R  Q  V  T  F  A  K  R  R  N  G  L  L  K  K  A  Y  E  L   35
121 TCTGTTCTTTGTGATGCTGAGGTTGCTCTCATCATCTTCTCCAATAGGGGAAAACTGTAC
    S  V  L  C  D  A  E  V  A  L  I  I  F  S  N  R  G  K  L  Y   55
181 GAGTTCTGCAGTAGCTCTAGCATGCTCAAGACATTAGAGAGGTACCAGAAGTGCAACTAC
    E  F  C  S  S  S  S  M  L  K  T  L  E  R  Y  Q  K  C  N  Y   75
241 GGAGCACCAGAGACCAATATATCCACACGAGAAGCACTGGAAATAAGTAGCCAACAAGAA
    G  A  P  E  T  N  I  S  T  R  E  A  L  E  I  S  S  Q  Q  E   95
301 TACTTGAAGCTTAAAGCACGTTACGAAGCATTACAGCGATCACAGAGAAATCTTCTTGGT
    Y  L  K  L  K  A  R  Y  E  A  L  Q  R  S  Q  R  N  L  L  G  115
361 GAAGATCTTGGCCCTTTGAATAGCAAGGAACTTGAATCACTTGAGAGGCAGCTTGATATG
    E  D  L  G  P  L  N  S  K  E  L  E  S  L  E  R  Q  L  D  M  135
421 TCACTGAAACAGATTCGATCAACTCGGACTCAGTTAATGTTGGATCAACTTACAGATCTT
    S  L  K  Q  I  R  S  T  R  T  Q  L  M  L  D  Q  L  T  D  L  155
481 CAGAGAAAGGAACATGCATTAAACGAAGCAAACAGAACCTTGAAACAAAGGTTGATGGAA
    Q  R  K  E  H  A  L  N  E  A  N  R  T  L  K  Q  R  L  M  E  175
541 GGAAGCCAACTAAATCTGCAGTGGCAACAAAATGCACAAGATATGGGCTACGGCCGGCAA
    G  S  Q  L  N  L  Q  W  Q  Q  N  A  Q  D  M  G  Y  G  R  Q  195
601 ACAACTCAAACTCAGGGCGATGGCTTTTTTCATCCTTTGGAATGTGAACCCACTTTGCAA
    T  T  Q  T  Q  G  D  G  F  F  H  P  L  E  C  E  P  T  L  Q  215
661 ATTGGGTATCAGAATGATCCAATAACAGTAGGAGGAGCAGGGCCCAGTGTGAATAACTAC
    I  G  Y  Q  N  D  P  I  T  V  G  G  A  G  P  S  V  N  N  Y  235
721 ATGGCTGGCTGGTTGCCTTGAAATTAAGCTCATTTCCGATAAGATTGATTATATAAACAT
    M  A  G  W  L  P  *                                          241
781 ATGCTCAATGTTTTTCCTATCATAAACACTCTCCTAATTTGTGTTATATGTTGTTTGCCG
841 AATTCTGGACTAATTTGGGATCCATAAGACAGACCCGTTATTGTTACTTAATCATAAACT
901 AGATTTCCCTGAGTGACTAATCACTAAAGCTTATTACTTTCCTCC(A)
```

FIG. 2

```
NT    1  MGRGRVELKRIENKINRQVTFAKRRNGLLKKAYELSVLCDAEVALIIFSN   50
         ||||:|||||||||||.|||||||||||||||||||:|||||||||||||.
OS    1  MGRGKVELKRIENKISRQVTFAKRRNGLLKKAYELSLLCDAEVALIIFSG   50

51  RGKLYEFCSSSSMLKTLERYQKCNYGAPETNISTREALEISSQQEYLKLK  100
         ||:|:||:|||:|.||||||..|||...:.. ...|    . |||||||
     51  RGRLFEFSSSSCMYKTLERYRSCNYNSQDAAAPENEI....NYQEYLKLK   96

101  ARYEALQRSQRNLLGEDLGPLNSKELESLERQLDMSLKQIRSTRTQLMLD  150
         .|  |  ||  .|||:|||||||||||. ||||  ||.|:::|||||||  :.|  :||
     97  TRVEFLQTTQRNILGEDLGPLSMKELEQLENQIEVSLKQIRSRKNQALLD  146

151  QLTDLQRKEHALNEANRTLKRLMEGSQ...LNLQWQQNAQDMG....YG  193
         ||  ||..||:.|.:  |:.|::| |.|.     |:: ||:.:..  |       .:
    147  QLFDLKSKEQQLQDLNKDLRKKLQETSAENVLHMSWQDGGGHSGSSTVLA  196

194  RQTTQTQGDGFFHPLECEPTLQIGYQNDPI.........TVGGAGPSVNN  234
         |. : ||      ||  :.:..|||||:::..              .:|:.  |.:
    197  DQPHHHQGLLHPHPDQGDHSLQIGYHHPHAHHHQAYMDHLSNEAADMVAH  246

235  YMAGWLP  241
         .  .: :|
    247  HPNEHIP  253
```

FIG. 3

GENE CONTROLLING FLORAL DEVELOPMENT AND APICAL DOMINANCE IN PLANTS

CROSS REFERENCE TO RELATED APPLICATION

This application is a continuation-in-part of co-pending U.S. patent application Ser. No. 08/323,449, filed on Oct. 14, 1994, incorporated herein by reference.

TECHNICAL FIELD

This invention is related to the field of compositions and methods for affecting plant floral development and more particularly to an isolated gene and its use in affecting the timing of the transition from vegetative to reproductive growth.

BACKGROUND ART

A majority of plants use environmental cues to regulate the timing of the transition from vegetative to reproductive growth in order to ensure synchronous flowering for successful outcrossing and to complete their sexual reproduction under favorable conditions (reviewed in Bernier et al., Plant Cell 5:1147–1155, 1993). The major environmental factors that control the transition are photoperiod, temperature, and nutrition.

In responding to these environmental factors, plants differ widely among species, among cultivars within species, and among stages of plant development within a cultivar. A short-day plant flowers when the day length is less than its critical length and a long-day plant flowers when the day length is longer than its critical length. Floral induction in a day-neutral species is unaffected by day-length, but occurs when the plant has attained a minimum amount of growth.

After completion of the basic vegetative phase, initiation of flowering is frequently dependent on the day length. The critical photoperiod is defined as the maximum day length that will induce a short-day plant to flower and the minimum day length that will induce a long-day plant to flower.

It has been postulated that a transmissible flowering signal is produced mainly in leaves and is transported to the shoot apex through the phloem. Grafting experiments have shown that leaves of photoperiodic plants produce promoters and inhibitors of flowering when exposed to favorable and unfavorable daylength regimes, respectively (Lang et al., Proc. Natl. Acad. Sci. USA 74:2412–2416, 1977). The nature of these transmissible signals is still controversial (O'Neill, Photochem. Photobiol. 56:789–801, 1992) and efforts to isolate the signaling substances have been unsuccessful. In addition, the target genes for these signals in the shoot apex have not been identified.

Significant effort has been expended in attempts to elucidate the underlying mechanisms controlling flower development in various dicotyledonous plant species (reviewed in Coen, Annu. Rev. Plant Physiol. Plant Mol. Biol. 42:241–279, 1991; and Gasser, Annu. Rev. Plant Physiol. Plant Mol. Biol. 42:621–649, 1991), leading to the isolation of a family of genes which encode regulatory proteins. These regulatory proteins include AGAMOUS (AG) (Yanofsky et al., Nature 346:35–39, 1990), APETELA I (API) (Mandel et al., Nature 360:273–277, 1992), and APETALA 3 (AP3) (Jack et al., Cell 68:683–697, 1992) in *Arabidopsis thaliana,* and DEFICIENS A (DEF A) (Sommer et al., EMBO J. 11:251–263, 1990), GLOBOSA (GLO) (Trobner et al., EMBO J. 11:4693–4704, 1992), SQUA- MOSA (SQUA) (Huijser et al., EMBO J. 11:1239–1249, 1992), and PLENA (PLE) (Bradley et al., Cell 72:85–95, 1993) in *Antirrhinum majus.*

Mutations in an AG or PLE gene result in homeotic alterations of the stamen and carpel. Genetic studies have shown that the DEF A, GLO and AP3 genes are essential for petal and stamen development. API and SQUA genes, which are expressed in young flower primordia, are necessary for the transition of an inflorescence meristem into a floral meristem. Sequence analysis of these genes has revealed that their gene products contain a conserved MADS-box region (Bradley et al., Cell 72:85–95, 1993; Huijser et al., EMBO J. 11:1239–1249, 1992; Jack et al., Cell 68:683–697, 1992; Mandel et al., Nature 360:273–277, 1992; Sommer et al., EMBO J. 11:251–263, 1990; Trobner et al., EMBO J. 11:4693–4704, 1992; Yanofsky et al., Nature 346:35–39, 1990), which is probably a DNA-binding domain (Schwarz-Sommer et al., EMBO J. 11:251–263, 1992).

Using these clones as probes, MADS-box genes have been isolated from other species including tomato (Mandel et al., Cell 71:133–143, 1992), tobacco (Kempin et al., Plant Physiol 103:1041–1046, 1993), petunia (Angenent et al., Plant Cell 4:983–993, 1992), *Brassica napus* (Mandel et al., Cell 71:133–143, 1992), and maize (Schmidt et al., Plant Cell 5:729–737, 1993).

Transgenic approaches have been employed to study the functional roles of MADS-box genes. Genetic complementation of the ag-2 mutant by the AG gene demonstrated that the ag-2 gene product is involved in stamen and carpel development (Yanofsky et al., Nature 346:35–39, 1990). Ectopic expression of the AG genes from *A. thaliana, B. napus,* petunia, tobacco, and tomato resulted in homeotic conversion of sepals to carpels and petals to stamens, mirroring the ap2 mutant phenotype (Kempin et al., Plant Physiol 103:1041–1046, 1993; Mandel et al., Cell 71:133–143, 1992; Mizukami and Ma, Cell 71:119–131, 1992; Pnueli et al., Plant Cell 6:163–173, 1994; Tsuchimoto et al., Plant Cell 5:843–853, 1993). These results support the hypothesis that AG and AP2 act in an antagonistic fashion.

Antisense approaches have also been used to reveal the functional role of the tomato MADS-box genes (Pnueli et al., Plant Cell 6:175–186, 1994; Pnueli et al., Plant Cell 6:163–173, 1994). Transgenic plants that express tomato AG antisense RNA display the ag mutant phenotypes. Antisense expression of the tomato TM5 MADS-box gene results in morphological changes in the three inner whorls of transgenic plants.

The timing of the transition from vegetative growth to flowering is one of the most important steps in plant development. This determines quality and quantity of most crop species since the transition determines the balance between vegetative and reproductive growth. It would therefore be highly desirable to have means to affect the timing of this transition. The present invention meets this and other needs.

SUMMARY OF THE INVENTION

The present invention provides compositions and methods related to the OsMADS1 gene of *Oryza sativa* and homologs thereof, such as the NtMADS3 gene of *Nicotiana tabacum,* and their use to alter the phenotype of a plant, including phenotypes related to the timing of the transition between vegetative and reproductive growth.

It is an object of the invention to provide isolated nucleic acids comprising at least 15 contiguous nucleic acids of (1) a native OsMADS1 or NtMADS3 gene, including alleles and homologs, or (2) variants of a native OsMADS1 gene, and preferably the full length native sequence of OsMADS1 or NtMADS3 as shown in FIGS. 1A or 2, respectively (SEQ ID NO:1 or SEQ ID NO:9, respectively). When expressed in a transgenic plant, the OsMADS1 gene produces at least one phenotype including (1) diminished apical dominance, (2) early flowering, (3) a partially or completely altered daylength requirement for flowering, (4) greater synchronization of flowering, or (5) a relaxed vernalization requirement. Variant forms of the OsMADS1 gene are preferably substantially similar in sequence to a native OsMADS1 gene and preferably comprise only silent or conservative substitutions to a native OsMADS1 gene sequence.

A further object of the invention is to provide host cells and transgenic plants in which an OsMADS1 gene or fragment thereof is introduced.

A further object of the invention is to provide purified polypeptides encoded by an OsMADS1 nucleic acid, e.g., by expression of an expression vector comprising an OsMADS1 gene or fragment thereof in a suitable host cell.

A further object of the invention is to provide probes and primers comprising a fragment of an OsMADS1 gene capable of hybridizing under stringent conditions to a native OsMADS1 gene sequence. Such probes and primers are useful, for example, in studying the structure and function of OsMADS1 genes and for obtaining homologs of the OsMADS1 gene from plants other than rice and tobacco.

The expression of an OsMADS1 transgene in transgenic plants of a long-day or short-day species, as noted above, can result in day-neutral phenotype, for example. Therefore, it is a further object of the invention to use such transgenic plants to produce multiple crops in a year, which otherwise cannot be accomplished under natural photoperiod conditions.

The foregoing and other objects and advantages of the invention will become more apparent from the following detailed description and accompanying drawings.

BRIEF DESCRIPTION OF THE DRAWINGS

FIG. 1A shows the nucleotide and deduced amino acid sequences of an OsMADS1 cDNA (SEQ ID NO:1). MADS-box and K-box regions are underlined. The positions of nucleotides and amino acids are shown on the left and right, respectively.

FIG. 1B provides a comparison of MADS-box regions, showing the alignment of the MADS-box sequence of OsMADS1 (residues 2–57; SEQ ID NO:2) with the MADS-box sequence of AP1, SQUA, AG, PLE, AP3, and DEF A (SEQ ID NOS:3, 4, 5, 6, 7, and 8, respectively). The asterisks indicate amino acids that are identical to corresponding amino acids of OsMADS1 (SEQ ID NO:2).

FIG. 2 shows the nucleotide and deduced amino acid sequence of the NtMADS3 cDNA (SEQ ID NO:9). The positions of nucleotides and amino acids are shown on the left and right, respectively.

FIG. 3 shows a comparison of the deduced NtMADS3 polypeptide sequence (top) and the deduced OsMADS polypeptide sequence (bottom).

DETAILED DESCRIPTION OF THE INVENTION

The present invention provides compositions and methods related to a "MADS-box" gene from rice, OsMADS1, and its homologs that are useful, for example, for producing dwarf plants and for affecting the timing of the transition from vegetative to reproductive growth in a wide variety of plants, including various dicotyledonous and monocotyledonous crop plants and tree species (see Schwarz-Sommer et al., Science 250:931–936, 1990 regarding "MADS-box" genes). OsMADS1 is a key regulatory factor determining the transition from shoot apex to floral meristem and is likely a target for action of flower induction signals.

The mechanism for the function of the rice OsMADS1 gene product is unknown. The OsMADS1 gene product may regulate the expression of genes that are involved in the induction of flowering, thus leading to the early flowering and dwarf phenotypes observed in day-neutral plants and overriding the photoperiod requirement for flowering in flowering plants of a species that is normally daylength-sensitive (i.e., a long-day and short-day species). The OsMADS1 polypeptide may, for example, act as a positive regulatory factor similar to AP1 or SQUA. Since the 35S promoter is active in most cell types, it is likely that OsMADS1 polypeptide produced under the control of the 35S promoter is accumulated in the shoot meristem and inflorescence meristem, where the AP1 (SQUA)-like gene is not yet activated. It has been reported that at least two genes, AP1 and LEAFY, are required for the transition of inflorescence meristem into floral meristem in Arabidopsis (Weigel et al., Cell 69:843–859, 1992). Similarly, SQUA and FLO-RICAULA are required for floral organ induction in *Antirrhinum majus* (Coen et al., Cell 63:1311–1322, 1990). It was determined that AP1 and SQUA belong to the MADS-box gene family (Coen et al., Cell 63:1311–1322, 1990; Weigel et al., Cell 69:843–859, 1992). If AP1 is normally expressed later than LEAFY, the ectopic expression of OsMADS1 may bypass the transient period required for normal floral organ development. Alternatively, the OsMADS1 protein may interact with a negative factor that normally inhibits flowering. It is also possible that a higher level of expression of OsMADS1 may enhance the response to flower-promoting signals.

No other MADS-box genes have been shown to induce early flowering and dwarfing and to override photoperiod requirements, for example. Although the early flowering and dwarf phenotypes were not apparent in transgenic plants in their juvenile state, axillary bud growth was initiated during the early stage of floral meristem development. The growing shoot apex is known to exert an influence over a range of developmental events, including axillary bud growth (Tamas, Hormonal regulation of apical dominance, In: Davies, ed., Plant Hormones and Their Role in Plant Growth and Development, Martinus Nijhoff Pub., Dordrecht, Netherlands, 1987, pp. 393–410). The effect is greatest early in plant development. As plants mature, the emergence of floral organs releases inhibition of the lateral buds and allows them to develop. The active substance responsible for apical dominance in a number of plant species has been identified as the plant growth regulator, indoleacetic acid (IAA). In transgenic plants expressing OsMADS1, the dwarf phenotype may be the result of altered hormonal status due to early flowering.

Use of the OsMADS1 Gene and its Homologs for Crop Improvement

According to the present invention, the OsMADS1 gene is useful, for the following purposes, among others. (Reference to the OsMADS1 gene is intended to encompass alleles, homologs, and variants as well).

Early flowering.

The timing of the transition between vegetative and reproductive growth is an important agronomic trait, serving as a crucial factor in determining crop yields. Expression of the OsMADS1 gene in transgenic plants makes it possible to affect the transition from vegetative to reproductive growth in a wide variety of plants, whether the plants are long-day, short-day, or day-neutral plants.

When the OsMADS1 gene is expressed in transgenic plants of day-neutral species, the resulting transgenic plants flower earlier than control plants. Transgenic long-day and short-day flowering plants expressing the OsMADS1 gene also flower earlier under permissive conditions than control plants. The compositions and methods according to the present invention therefore permit one to reduce the length of the vegetative growth stage of cereal, fruit, vegetable, floricultural, and other crop species.

Producing dwarf plant varieties.

Although it has been possible to enhance the harvest index in grain crops by the use of dwarfing genes, the isolation of these genes producing dwarf phenotypes has been difficult.

Transgenic plants comprising a OsMADS1 transgene are shorter than controls. Expression of an OsMADS1 transgene apparently causes no significant change in the rate of photosynthesis or the total mass of the plant. Therefore, the OsMADS1 gene is useful for producing dwarf plant varieties for a variety of plants including cereal, fruit, and floricultural species.

Synchronizing reproductive growth.

Transgenic plants expressing the OsMADS1 transgene flower more synchronously than controls. Therefore, the gene can be used for crops for which synchronized harvesting is economically beneficial, allowing more effective use of mechanized harvesting of fruit species or the production of floricultural species having improved flower quality, for example.

Producing day-neutral plant varieties.

Expression of an OsMADS1 transgene in daylength-sensitive (i.e., long-day or short-day) plants at least partially overrides the photoperiod requirement for flowering and can completely override the photoperiod requirement. By introducing such a transgene into a wide variety of photoperiod-sensitive crop species, including, but not limited to rice and soybeans, these plants effectively become day-neutral, permitting multiple crops to be grown per year. For example, flowers can be induced the year-round by introducing an OsMADS1 transgene into floricultural species such as chrysanthemum and orchid.

Delaying flowering and fruiting.

By suppressing the expression of the OsMADS1 gene by conventional approaches, e.g., by employing antisense, co-suppression, gene replacement, or other conventional approaches to suppressing plant gene expression, flowering and fruiting can be delayed. Delayed reproductive growth can thereby increase the length of the vegetative growth stage and cause the plants to grow faster, since the energy used for development of flowers and seeds can be saved for vegetative growth. Thus, delaying or eliminating reproductive growth results in a higher yield of vegetable species such as spinach, radish, cabbage, or tree species. In addition, such plants will be more desirable for as garden and street species, since their production of pollen allergens can be reduced or eliminated.

Overcoming the vernalization requirement.

The OsMADS1 gene is useful for overriding the vernalization requirement of certain plant species. It is likely that the OsMADS1 gene is the last (or almost last) gene expressed in the flower induction pathway. Therefore, induction of flowering of transgenic plants that constitutively express the OsMADS1 gene becomes insensitive to temperature.

Growing plants in space.

Plants grown extraterrestrially are preferably insensitive to photoperiod and temperature for flowering. Transgenic plants carrying the OsMADS1 gene would be expected to flower in the extremely abnormal growth conditions found in a space shuttle or space station.

Cloning and analysis of homologs of the OsMADS1 gene in other plants.

The availability of the OsMADS1 gene and its sequence makes it possible to obtain homologs of the OsMADS1 gene in other organisms by conventional methods, through the use of nucleic acid and antibody probes and DNA primers based on the OsMADS1 sequence, as described in greater detail below. These probes and primers are also useful in research on the patterns of expression and structure-function relationships for rice OsMADS1 and its homologs, and for determining the interaction of these genes with other plant genes involved in floral development, for example.

DEFINITIONS AND METHODS

The following definitions and methods are provided to better define the present invention and to guide those of ordinary skill in the art in the practice of the present invention. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994.

The term "plant" encompasses any plant and progeny thereof. The term also encompasses parts of plants, including seed, cuttings, tubers, fruit, flowers, etc.

A "reproductive unit" of a plant is any totipotent part or tissue of the plant from which one can obtain a progeny of the plant, including, for example, seeds, cuttings, buds, bulbs, somatic embryos, etc.

"Natural photoperiod conditions" are photoperiod (i.e., daylength) conditions as provided by sunlight at a given location, whether under field conditions. A photoperiod provided by artificial lighting but having a daylength approximating that of sunlight would also be considered a natural photoperiod condition.

Nucleic Acids

Nucleic acids useful in the practice of the present invention comprise the isolated rice OsMADS1 gene, its homologs in other plant species, and fragments and variants thereof.

The term "OsMADS1" gene refers to a plant gene that contains a MADS-box sequence, and preferably also a K-box sequence, and that is associated with one or more of the following phenotypes when expressed as a transgene in transgenic plants: (1) diminished apical dominance (as shown, for example, by dwarf stature); (2) early flowering; (3) altered daylength requirement for flowering; (4) greater synchronization of flowering; and (5) relaxed vernalization requirement. This term relates primarily to an isolated OsMADS1 coding sequence, it also encompasses sequences comprising genomic sequences flanking the OsMADS1 coding sequence that are operably linked to the coding sequence, including regulatory elements and/or intron sequences. Although the term "OsMADS1 gene" most properly applies to the rice OsMADS1 gene as shown in FIG. 1A (SEQ ID NO:1), it is also intended to encompass alleles of the rice OsMADS1 gene and homologs thereof from other plant species, such as the NtMADS3 gene of *Nicotiana tabacum*, as shown in FIG. 2 (SEQ ID NO:9). The term "OsMADS1 gene" also encompasses "variant" forms of the gene (as detailed below) that have substantial homology to an OsMADS1 sequence and OsMADS1 biological activity.

The term "native" refers to a naturally-occurring nucleic acid or polypeptide, including a wild-type sequence and an allele thereof.

A "homolog" of the OsMADS1 gene is a native gene sequence isolated from a plant species other than *Oriza sativa* that has at least one of the biologically activities of OsMADS1, e.g., affecting apical dominance in transgenic plants, etc., as discussed above.

The nucleic acids of the present invention can be free in solution or attached by conventional means to a solid support, such as a hybridization membrane (e.g., nitrocellulose or nylon), a bead, or other solid supports known in the art.

"Isolated".

An "isolated" nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid-purification methods. The term also embraces nucleic acids prepared by recombinant expression in a host cell as well as chemically synthesized nucleic acids.

DNA constructs incorporating an OsMADS1 gene or fragment thereof according to the present invention preferably place the OsMADS1 protein coding sequence under the control of an operably linked promoter that is capable of expression in a plant cell. Various promoters suitable for expression of heterologous genes in plant cells are known in the art, including constitutive promoters, e.g. the cauliflower mosaic virus (CaMV) 35S promoter, which is expressed in many plant tissues, organ- or tissue-specific promoters, and promoters that are inducible by chemicals such as methyl jasminate, salicylic acid, or Safener, for example.

Plant transformation and regeneration.

In addition to the methods for plant transformation and regeneration described in the Examples below for making transgenic plants, other well-known methods can be employed.

Fragments probes, and primers.

A fragment of an OsMADS1 nucleic acid according to the present invention is a portion of the nucleic acid that is less than full-length and comprises at least a minimum length capable of hybridizing specifically with an OsMADS1 nucleic acid according to the present invention (or a sequence complementary thereto) under stringent conditions as defined below. The length of such a fragment is preferably 15 nucleotides or more, although a shorter nucleic acid can be employed as a probe or primer if it is shown to specifically hybridize under stringent conditions with a target nucleic acid by methods well known in the art.

Nucleic acid probes and primers can be prepared based on nucleic acids according to the present invention, e.g., the OsMADS1 gene of FIG. 1A (SEQ ID NO:1) or the NtMADS3 gene of FIG. 2 (SEQ ID NO:9). A "probe" comprises an isolated nucleic acid attached to a detectable label or reporter molecule well known in the art. Typical labels include radioactive isotopes, ligands, chemiluminescent agents, and enzymes.

"Primers" are short nucleic acids, preferably DNA oligonucleotides 15 nucleotides or more in length, which are annealed to a complementary target DNA strand by nucleic acid hybridization to form a hybrid between the primer and the target DNA strand, then extended along the target DNA strand by a polymerase, preferably a DNA polymerase. Primer pairs can be used for amplification of a nucleic acid sequence, e.g., by the polymerase chain reaction (PCR) or other nucleic-acid amplification methods well known in the art. PCR-primer pairs can be derived from the sequence of a nucleic acid according to the present invention, for example, by using computer programs intended for that purpose such as Primer (Version 0.5,© 1991, Whitehead Institute for Biomedical Research, Cambridge, Mass.).

Methods for preparing and using probes and primers are described, for example, in Sambrook et al., Molecular Cloning: A Laboratory Manual, 2nd ed., vol. 1–3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1987 (with periodic updates); and Innis et al., PCR Protocols: A Guide to Methods and Applications, Academic Press: San Diego, 1990.

Probes or primers can be free in solution or covalently or noncovalently attached to a solid support by standard means.

Substantial similarity.

A first nucleic acid is "substantially similar" to a second nucleic acid if, when optimally aligned (with appropriate nucleotide insertions or deletions) with the other nucleic acid (or its complementary strand), there is nucleotide sequence identity in at least about 75%–90% of the nucleotide bases, and preferably greater than 90% of the nucleotide bases. ("Substantial sequence complementarity" requires a similar degree of sequence complementarity.) Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

Operably linked.

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant".

A "recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Techniques for nucleic-acid manipulation are described generally in, for example, Sambrook et al. (1989) and Ausubel et al. (1987, with periodic updates).

Preparation of recombinant or chemically synthesized nucleic acids; vectors, transformation, host cells.

Large amounts of a nucleic acid according to the present invention can be produced by recombinant means well known in the art or by chemical synthesis.

Natural or synthetic nucleic acids according to the present invention can be incorporated into recombinant nucleic-acid constructs, typically DNA constructs, capable of introduction into and replication in a host cell. Usually the DNA constructs will be suitable for replication in a unicellular host, such as *E. coli* or other commonly used bacteria, but can also be introduced into yeast, mammalian, plant or other eukaryotic cells.

Preferably, such a nucleic-acid construct is a vector comprising a replication system recognized by the host. For the practice of the present invention, well-known compositions and techniques for preparing and using vectors, host cells, introduction of vectors into host cells, etc. are employed, as discussed, inter alia, in Sambrook et al., 1989, or Ausubel et al., 1987.

A cell, tissue, organ, or organism into which has been introduced a foreign nucleic acid, such as a recombinant vector, is considered "transformed" or "transgenic." The DNA construct comprising an OsMADS1 DNA sequence according to the present invention that is present in a transgenic host cell, particularly a transgenic plant, is referred to as a "transgene." The term "transgenic" or "transformed" when referring to a cell or organism, also includes (1) progeny of the cell or organism and (2) plants produced from a breeding program employing such a "transgenic" plant as a parent in a cross and exhibiting an altered phenotype resulting from the presence of the recombinant OsMADS1 DNA construct.

Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

Nucleic-Acid Hybridization; "Stringent Conditions"; "Specific".

The nucleic-acid probes and primers of the present invention hybridize under stringent conditions to a target DNA sequence, e.g., to the rice OsMADS1 gene and its homologs in other plant species.

The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989 at 9.52–9.55. See also, Sambrook et al., 1989 at 9.47–9.52, 9.56–9.58; Kanehisa, Nuc. Acids Res. 12:203–213, 1984; and Wetmur and Davidson, J. Mol. Biol. 31:349–370, 1968.

Regarding the amplification of a target nucleic-acid sequence (e.g., by PCR) using a particular amplification primer pair, stringent conditions are conditions that permit the primer pair to hybridize only to the target nucleic-acid sequence to which a primer having the corresponding wild-type sequence (or its complement) would bind.

Nucleic-acid hybridization is affected by such conditions as salt concentration, temperature, or organic solvents, in addition to the base composition, length of the complementary strands, and the number of nucleotide-base mismatches between the hybridizing nucleic acids, as will be readily appreciated by those skilled in the art.

When referring to a probe or primer, the term "specific for (a target sequence)" indicates that the probe or primer hybridizes under stringent conditions only to the target sequence in a given sample comprising the target sequence.

Nucleic-acid amplification.

As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications,* Innis et al. eds., Academic Press, San Diego, 1990.

In situ hybridization.

A number of techniques have been developed in which nucleic-acid probes are used to locate specific DNA sequences on intact chromosomes in situ, a procedure called "in situ hybridization." See, e.g., Pinkel et al., Proc. Natl. Acad. Sci. USA 85:9138–9142, 1988 (regarding fluorescence in situ hybridization), and Lengauer et al., Hum. Mol. Genet. 2:505–512, 1993 (regarding "chromosomal bar codes"). Well-known methods for in situ hybridization and for the preparation of probes or primers for such methods are employed in the practice of the present invention, including direct and indirect in situ hybridization methods.

Methods of making cDNA clones encoding OsMADS1 or homologs thereof.

Based upon the availability of the OsMADS1 and NtMADS3 cDNAs and the nucleotide sequences thereof, as disclosed herein, other OsMADS1 genes (e.g., alleles and homologs of OsMADS1 and NtMADS3) can be readily obtained from a wide variety of plants by cloning methods known in the art.

For example, one or more primer pairs based on the OsMADS1 sequence can be used to amplify such OsMADS1 genes or their homologs by the polymerase chain reaction (PCR). Alternatively, the disclosed OsMADS1 cDNA or fragments thereof can be used to probe a cDNA or genomic library made from a given plant species.

Cloning of the OsMADS1 Genomic Gene and Homologs Thereof.

The availability of the OsMADS1 cDNA sequence enables those skilled in the art to obtain a genomic clone corresponding to the OsMADS1 cDNA (including the promoter and other regulatory regions and intron sequences) and the determination of its nucleotide sequence by conventional methods. Such an OsMADS1 genomic clone and sequences derived therefrom are useful, for example, for studies of the expression of the OsMADS1 gene.

Nucleotide-Sequence Variants of OsMADS1 cDNA and Amino Acid Sequence Variants of OsMADS1 Protein.

Using the nucleotide and the amino-acid sequence of the OsMADS1 protein disclosed herein, those skilled in the art can create DNA molecules and polypeptides that have minor variations in their nucleotide or amino acid sequence. "Variant" DNA molecules are DNA molecules containing minor changes in the native OsMADS1 sequence, i.e., changes in which one or more nucleotides of a native OsMADS1 sequence is deleted, added, and/or substituted while substantially maintaining OsMADS1 biological activity. Variant DNA molecules can be produced, for example, by standard DNA mutagenesis techniques or by chemically synthesizing the variant DNA molecule. Such variants do not change the reading frame of the protein-coding region of the nucleic acid and encode a protein having no or only minor changes in OsMADS1 biological function. Preferably, the mutations made in the native OsMADS1 sequence do not create complementary regions that could produce secondary mRNA structure (see, e.g., EP 75,444A).

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant nucleic acids according to the present invention are "silent" or "conservative" variants. "Silent" variants are variants of a native rice OsMADS1 sequence or a homolog thereof in which there has been a substitution of one or more base pairs but no change in the amino-acid sequence of the polypeptide encoded by the sequence. "Conservative" variants are variants of the native rice OsMADS1 sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. A number of conservative amino acid substitutions are listed in Table 3. In addition, one or more codons encoding cysteine residues can be substituted for, resulting in a loss of a cysteine residue and affecting disulfide linkages in the OsMADS1 polypeptide.

TABLE 1

| Original Residue | Conservative Substitutions |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those in Table 1, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Polypeptides

The term "OsMADS1 protein (or polypeptide)" refers to a protein encoded by an OsMADS1 gene, including alleles and homologs of OsMADS1, or by a variant of the OsMADS1 gene, having OsMADS1 biological activity. An OsMADS1 polypeptide can be isolated from a natural source, produced by the expression of a recombinant OsMADS1 nucleic acid, or be chemically synthesized. Techniques for chemical synthesis of polypeptides are described, for example, in Merrifield, J. Amer. Chem. Soc. 85:2149–2156, 1963.

Polypeptide sequence homology.

Ordinarily, the polypeptides encompassed by the present invention are at least about 70% homologous to a native OsMADS1 polypeptide, preferably at least about 80% homologous, and more preferably at least about 95% homologous. Such homology is considered to be "substantial homology," although more important than shared amino-acid sequence homology can be the common possession of characteristic structural features and the retention of characteristic biological activity.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated," "Purified," "Homogeneous" Polypeptides.

A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized or recombinant (i.e., the product of the expression of a recombinant nucleic acid, even if expressed in a homologous cell type) is considered to be isolated. A monomeric polypeptide is isolated when at least 60–90% by weight of a sample is composed of the polypeptide, preferably 95% or more, and more preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other methods known in the art.

Protein purification.

The polypeptides of the present invention can be purified by any of the means known in the art. Various methods of protein purification are described, e.g., in Guide to Protein Purification, ed. Deutscher, Meth. Enzymol. 185, Academic Press, San Diego, 1990; and Scopes, Protein Purification: Principles and Practice, Springer Verlag, New York, 1982.

Variant forms of OsMADS1 polypeptides; labeling.

Encompassed by the claimed OsMADS1 polypeptides are variant polypeptides in which there have been substitutions, deletions, insertions or other modifications of the native OsMADS1 polypeptide. The variants substantially retain structural and/or biological characteristics and are preferably silent or conservative substitutions of one or a small number of contiguous amino acid residues.

The native OsMADS1 polypeptide sequence can be modified by conventional methods, e.g., by acetylation, carboxylation, phosphorylation, glycosylation, ubiquitination, and labeling, whether accomplished by in vivo or in vitro enzymatic treatment of an OsMADS1 polypeptide or by the synthesis of an OsMADS1 polypeptide using modified amino acids.

There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Molecular Cloning: A Laboratory Manual, 2nd ed., vol. 1–3, ed. Sambrook et al., Cold Spring Harbor Laboratory Press: Cold Spring Harbor, N.Y., 1989; and Current Protocols in Molecular Biology, ed. Ausubel et al., Greene Publishing and Wiley-Interscience: New York, 1987 (with periodic updates).

Polypeptide Fragments.

The present invention also encompasses fragments of OsMADS1 polypeptides that lack at least one residue of a native full-length OsMADS1 polypeptide yet retain at least one of the biological activities characteristic of rice OsMADS1. For example, the fragment can cause early flowering or dwarf phenotypes when expressed as a transgene in a host plant or possession of a characteristic immunological determinant. As an additional example, an immunologically active fragment of an OsMADS1 polypeptide is capable of raising OsMADS1-specific antibodies in a target immune system (e.g., murine or rabbit) or of competing with OsMADS1 for binding to OsMADS1-specific antibodies, and is thus useful in immunoassays for the presence of OsMADS1 polypeptides in a biological sample. Such immunologically active fragments typically have a minimum size of 7 to 17 amino acids.

Fusion polypeptides.

The present invention also provides fusion polypeptides including, for example, heterologous fusion polypeptides, i.e., an OsMADS1 polypeptide sequence or fragment thereof and a heterologous polypeptide sequence, e.g., a sequence from a different polypeptide. Such heterologous fusion polypeptides thus exhibit biological properties (such as ligand-binding, catalysis, secretion signals, antigenic determinants, etc.) derived from each of the fused sequences. Fusion partners include, for example, immunoglobulins, beta galactosidase, trpE, protein A, beta lactamase, alpha amylase, alcohol dehydrogenase, yeast alpha mating factor, and various signal and leader sequences which, e.g., can direct the secretion of the polypeptide. Fusion polypeptides are typically made by the expression of recombinant nucleic acids or by chemical synthesis.

Polypeptide sequence determination.

The sequence of a polypeptide of the present invention can be determined by various methods known in the art. In order to determine the sequence of a polypeptide, the polypeptide is typically fragmented, the fragments separated, and the sequence of each fragment determined. To obtain fragments of an OsMADS1 polypeptide, the polypeptide can be digested with an enzyme such as trypsin, clostripain, or Staphylococcus protease, or with chemical agents such as cyanogen bromide, o-iodosobenzoate, hydroxylamine or 2-nitro-5-thiocyanobenzoate. Peptide fragments can be separated, e.g., by reversed-phase high-performance liquid chromatography (HPLC) and analyzed by gas-phase sequencing.

Polypeptide coupling to a solid phase support.

The polypeptides of the present invention can be free in solution or coupled to a solid-phase support, e.g., nitrocellulose, nylon, column packing materials (e.g., Sepharose beads), magnetic beads, or glass wool.

Antibodies

The present invention also encompasses polyclonal and/or monoclonal antibodies capable of specifically binding to OsMADS1 polypeptides and fragments thereof, produced by conventional methods. Such antibodies are raised against an OsMADS1 polypeptide and are capable of distinguishing the OsMADS1 polypeptide from other polypeptides.

An immunological response is usually assayed with an immunoassay. Normally such immunoassays involve some purification of a source of antigen, for example, produced by the same cells and in the same fashion as the antigen was produced.

For the preparation and use of antibodies according to the present invention, including various immunoassay techniques and applications, see, e.g., Goding, Monoclonal Antibodies: Principles and Practice, 2d ed, Academic Press, New York, 1986; and Harlow and Lane, Antibodies: A Laboratory Manual, Cold Spring Harbor Laboratory, Cold Spring Harbor, N.Y., 1988. OsMADS1-specific antibodies are useful, for example in purifying OsMADS1 polypeptides from a biological sample, such as a host cell expressing recombinant OsMADS1 polypeptides; in cloning OsMADS1 homologs from rice or other plant species from an expression library; as antibody probes for protein blots and immunoassays; etc.

Frequently, the polypeptides and antibodies will be labeled by joining, either covalently or noncovalently, a substance which provides for a detectable signal. A wide variety of labels and conjugation techniques are known. Suitable labels include radionuclides, enzymes, substrates, cofactors, inhibitors, fluorescent agents, chemiluminescent agents, magnetic particles and the like.

The invention will be better understood by reference to the following Examples, which are intended to merely illustrate the best mode now known for practicing the invention. The scope of the invention is not to be considered limited thereto, however.

EXAMPLES

Example 1

Isolation and Analysis of a MADS-Box Gene from Rice, OsMADS1

Bacterial Strains, Plant Materials, and Plant Transformation.

*Escherichia coli* MC1000 (ara, leu, lac, gal, str) was used as the recipient for routine cloning experiments. Rice (*Oryza sativa* L. cv. M201) plants were grown in a growth chamber at 26° C. with 10.5-hr day cycle.

cDNA Library Construction and Molecular Characterization.

A cDNA library was constructed using the λZapII vector (Stratagene, La Jolla, Calif.) and poly(A)+ mRNA isolated from rice flowers. An adapter containing EcoRI and NotI sites (Pharmacia LKB Biotechnology, Piscataway, N.J.) was used to ligate the vector and cDNA. The library was divided into 20 sublibraries and amplified in an *E. coli* host strain, XL-1 Blue [F'::Tn10 pro+B+, lacIq, (lac Z)MI5/recAJ.

endAI, gyrA96 (Nar), thi, hsdR17(rk⁻, mk⁺), sup44, reLA1, lac] (Stratagene, La Jolla, Calif.).

Plaque hybridization was performed with $10^5$ plaques that were lifted onto nitrocellulose membranes. The plasmid pBluescript containing the OsMADS1 cDNA was rescued in vivo from the bacteriophage λ using fl helper phage, R408 (Stratagene, La Jolla, Calif.). Both strands of the cDNA inserts were sequenced by the dideoxynucleotide chain-termination method using double-stranded DNA as a template (Sanger et al., Proc. Natl. Acad. Sci. USA 74:5463–5467, 1977).

Southern and Northern Blot Analyses.

Genomic DNA was prepared from two-week-old rice seedlings by the CTAB (cetyltrimethylammonium bromide) method (Rogers and Bendich, Extraction of DNA from plant tissues, In: Gelvin and Schilperoort, eds., Plant Molecular Biology Manual, Kluwer Academic, Dordrecht, Belgium, 1988, pp. A6/1–10). Four μg of DNA were digested with appropriate restriction enzymes, separated on a 0.7% agarose gel, blotted onto a nylon membrane, and hybridized with a $^{32}$P-labeled probe labeled by the random-priming method (Sambrook et al., Molecular Cloning: A Laboratory Manual, Cold Spring Harbor Laboratory Press, Cold Spring Harbor, N.Y., 1989). Ten μg of total RNA isolated by the guanidium thiocyanate method were used for the northern analysis (id.).

In situ Localization.

Rice flowers were dehydrated with ethanol, fixed (1.4% glutaraldehyde, 2% paraformaldehyde, 50 mM PIPES, pH 7.2), and embedded in paraffin. Eight-μm sections were attached to gelatin-coated glass slides and hybridized with $^{35}$S-labeled antisense RNA (Cox and Goldberg, Analysis of plant gene expression, In: Shaw, ed., Plant Molecular Biology: A Practical Approach, IRL Press, Oxford, 1988, pp. 1–34). The RNA probe was prepared by in vitro transcription using pBluescript carrying the OsMADS1 cDNA clone as a template. The sections were coated with an X-ray emulsion film and exposed for four days. The samples were stained with 0.5% toluidine blue to visualize tissue sections. Photographs were taken with a bright-field microscope.

Results.

A cDNA clone, OsMADS1, was isolated by screening a λ ZapII cDNA library prepared from immature rice flower mRNA using mixed probes of different MADS-box cDNA clones isolated from Arabidopsis (Ma et al., Genes Dev. 5:484–495, 1991; Yanofsky et al., Nature 346:35–39, 1990), Brassica (Mandel et al., Cell 71:133–143, 1992), tobacco (Kempin et al., Plant Physiol. 103:1041–1046, 1933), and tomato (Pnueli et al., Plant J. 1:255–266, 1991).

DNA sequence analysis showed that the rice clone encodes a protein of 257 amino-acid residues (FIG. 1A; SEQ ID NO:1). The deduced amino-acid sequence contains the conserved MADS-box domain between amino acids 2 and 57 (FIG. 1B; SEQ ID NO:2). A second domain present in MADS-box proteins, the "K-box," is located between residues 90 and 143. The OsMADS1 clone appears to be nearly full length, since the estimated transcript length by northern hybridization analysis is similar to that of the cDNA clone. The conserved MADS-box region is located immediately after the start methionine codon in the rice gene, as has been observed in most MADS-box genes. Therefore it is unlikely that the rice clone encodes a truncated protein.

These observations indicate that OsMADS1 is a member of the MADS-box gene family. Among characterized MADS-box proteins, the OsMADS1 amino-acid sequence is most homologous to AP1 (44.4% identity) and SQUA (42.6% identity). In addition, OsMADS1 shows extensive similarity to the functionally anonymous Arabidopsis MADS-box genes AGL2 (56.2% identity) and AGL4 (55.4% identity).

To determine the number of MADS-box genes present in rice, Southern blot analysis was performed on rice DNA digested with EcoRI (E), HindIII (H), or PstI (P), fractionated on a 0.7% agarose gel, and hybridized with a probe prepared from the entire OsMADS1 cDNA or an OsMADS1 cDNA probe lacking the conserved MADS-box region. More than ten restriction fragments hybridized with the entire cDNA probe, whereas a single fragment was detected by a probe lacking the conserved MADS-box region. This result indicates that the rice genome contains a large number of genes encoding MADS-box proteins, similar to what is observed in other plant species (Angenent et al., Plant Cell 4:983–993, 1992; Ma, Genes Dev. 5:484–495, 1991; Pnueli et al., Plant J. 1:255–266, 1991; Schmidt et al., Plant Cell 5:729–737, 1993).

Northern blot analyses were conducted to study the expression pattern of the OsMADS1 gene in rice. Ten-μg samples of total RNA isolated from leaf (L) and root (R) of two-week-old seedlings, and anther (A), carpel (C), and palea/lemma (P) of anthesis-stage flowers was hybridized with the OsMADS1 probe lacking the MADS domain. Ethidium bromide staining of 25S and 18S rRNAs demonstrated equal amounts of RNA loading. To determine the pattern of temporal expression of OsMADS1 during flower development, twenty μg of total RNA was isolated from rice flowers at different developmental stages: young inflorescence (panicle size<1 cm), young flowers (panicle size=1 to 6 cm), flowers at the early vacuolated pollen stage, and flowers at the late vacuolated pollen stage. This RNA was used for detection of OsMADS1 gene expression. RNA samples were hybridized with the probe lacking the conserved MADS-box region in order to avoid cross-hybridization with other MADS-box genes and thus to observe the specific expression pattern of the gene. OsMADS1 transcripts were present in the palea, lemma, and carpel, but not in the anther or vegetative organs. The gene was active during the young inflorescence stage and expression continued into the early and late vacuolated pollen stages.

The localization of the OsMADS1 transcript in rice flowers and phenotypes of transgenic tobacco plants expressing OsMADS1 were determined by in situ hybridization experiments using longitudinal sections of young inflorescence, and cross sections of the upper and lower rice flower at the vacuolated pollen stage (anther, filament, flower primordial lemma, ovary, palea, sheath, and sterile lemma). 8-μm sections were hybridized with $^{35}$S-labeled antisense RNA lacking the MADS-box domain. The sections were coated with an X-ray emulsion film and exposed for four days. The samples were stained with 0.5% toluidine blue to visualize tissue sections which show negative expression of the gene. A sense probe did not show any hybridization above the background level. These in situ experiments revealed that the OsMADS1 transcript was uniformly present in young flower primordia during early flower development and later became localized in certain floral organs. In young inflorescences, strong hybridization signals were detected in flower primordia but not in other tissues. In vacuolated pollen-stage flowers, OsMADS1 mRNA was detected in the palea, lemma, and ovary. However, the hybridization signal was not uniform in these tissues. In particular, the tissues near the palea/lemma junction and the palea tissues covered by lemma exhibited little or no expression of the gene. No significant signal was observed in the anther, filament, or sterile lemma. These results indicate that the OsMADS1 gene is preferentially expressed in certain floral tissues, as has been observed with most MADS-box genes.

The expression pattern of the OsMADS1 gene closely resembled that of AP1 and SQUA (Juijser et al., EMBO J. 11:1239–1249, 1992; Mandel et al., Nature 360:273–277, 1992). Flower-specific expression is also common for other MADS-box genes (Angenant et al., Plant Cell 4:983–993, 1992; Jack et al., Cell 68:683–697, 1992; Kempin et al., Plant Physiol. 103:1041–1046, 1993; Ma et al., Genes Dev. 5:484–495, 1991; Mandel et al., Nature 360:273–277, 1992; Pnueli et al., Plant J. 1:255–266, 1991; Schmidt et al., Plant Cell 5:729–737, 1993; Sommer et al., EMBO J. 9:605–613, 1990; Tsuchimoto et al., Plant Cell 5:843–853, 1993).

Nine independent clones that contain the conserved MADS-box have been isolated.

Example 2

Expression of OsMADS1 in Transgenic Tobacco Plants Results in Early Flowering and Dwarf Phenotypes Bacterial Strains, Plant Materials, and Plant Transformation.

*Agrobacterium tumefaciens* LBA4404 (Hoekema et al., Nature 303:179–181, 1983), containing the Ach5 chromosomal background and a disarmed helper-Ti plasmid pAL4404, was used for transformation of tobacco plants (*Nicotiana tabacum* L. cv. Petit Havana SR1) by the co-cultivation method (An et al., Binary Vectors, In: Gelvin and Schilperoort, eds., Plant Molecular Biology Manual, Kluwer Academic, Dordrecht, Belgium, 1988, pp. A3/1–19). Transgenic plants were maintained in a greenhouse.

Results.

Ectopic expression of floral homeotic genes alters floral organ identity in homologous (Kempin et al., Plant Physiol. 103:1041–1046, 1993; Mizukami and Ma, Cell 71:119–131, 1992; Pnueli et al., Plant Cell 6:163–173, 1994; Tsuchimoto et al., Plant Cell 5:843–853, 1993) and heterologous systems (Mandel et al., Cell 71:133–143, 1992).

In order to characterize the functional role of OsMADS1, tobacco plants were used as a heterologous expression system. The cDNA clone encoding the entire OsMADS1 coding region was placed under the control of cauliflower mosaic virus 35S promoter (Benfey and Chua, Science 250:959–966, 1990) and transcript 7 terminator using a binary vector pGA748, which is a derivative of pGA643 (An et al., Binary Vectors, In: Gelvin and Schilperoort, eds., Plant Molecular Biology Manual, Kluwer Academic, Dordrecht, Belgium, 1988, pp. A3/1–19). The chimeric molecule (pGA1209) was transferred to tobacco (*Nicotiana tabacum* cv. Petite Havana SR1) plants using the Agrobacterium-mediated Ti plasmid vector system (An et al., Binary Vectors, In: Gelvin and Schilperoort, eds., Plant Molecular Biology Manual, Kluwer Academic, Dordrecht, Belgium, 1988, pp. A3/1–19). Twenty independent transgenic plants were studied.

Most of the primary transgenic plants flowered much earlier than control plants that were transformed with the Ti plasmid vector alone. The transgenic plants were significantly shorter and contained several lateral branches. These phenotypes were inherited to the next generation as a dominant Mendelian trait.

Northern-blot analysis was conducted on seven transgenic plants which displayed the early flowering phenotype. Transcripts from a control plant and seven different transgenic plants exhibiting the early flowering and dwarf phenotypes were sampled for preparation of total RNA from leaves and flowers. Twenty µg of total RNA was hybridized with $^{32}$P-labeled probe prepared from the OsMADS1 cDNA lacking the MADS domain. The results showed that all of the transgenic plants accumulated the OsMADS1 transcripts in both vegetative and reproductive organs. Although there were significant differences in gene expression among the transgenic plants, the relative expression level was similar between the leaf and flower. Transgenic plant #7, which displayed the most severe symptoms, accumulated the highest level of the transcript. Plants #4, #5, #6, with less severely altered phenotypes, expressed the gene at reduced levels, indicating that the level of OsMADS1 RNA correlated with phenotype.

However, progeny from the same parent displayed phenotypic variation. The basis of this variation was investigated with T1 offspring of the transgenic plant #2 in which the transgene segregates as a single locus. OsMADS1 homozygotes were much shorter (34.2±0.8 cm) compared to heterozygotes (51.6±1.4 cm), while the wild-type tobacco plants were 119.8±2.2 cm. The homozygotes flowered two days earlier than the heterozygotes and eight days earlier than wild type plants. This result indicates that the variation was due to gene dosage.

Table 2 summarizes characteristics of four independently transformed plants from the T1 generation. Seeds were collected from selfed fruits of the primary transgenic plants (T0 generation). The seeds were germinated in a peat pellet and grown for two weeks at 16 hr light/8 hr dark cycles under fluorescent lights. The resulting T1 plants were grown under greenhouse conditions. Ten to twenty plants were analyzed for each transgenic line. Standard errors are shown in parentheses. Progeny carrying the transgenes were identified by visually scoring T2 seedlings for kanamycin resistance. The kanamycin-sensitive segregants were used as controls (C). Days to flowering include the time from seed germination to the first anthesis. Height and internode length were measured when fruits were fully developed (90 days postgermination). The data in Table 2 show that transgenic plants flowered 7 to 10 days earlier than wild-type plants and their height and internode length appear to be significantly reduced.

TABLE 2

Comparison of phenotypes of transgenic plants with non-transformed control

| Transgenic Line (#) | Days to Flowering | Height (cm) | Internode Length (cm) |
|---|---|---|---|
| 1 | 53.0 (2.0) | 61.2 (5.8) | 5.7 (0.5) |
| 2 | 54.2 (0.3) | 47.6 (1.9) | 4.6 (0.2) |
| 3 | 53.0 (0.4) | 64.3 (3.5) | 5.8 (0.3) |
| 4 | 50.6 (0.9) | 40.2 (4.4) | 3.5 (0.3) |
| C | 61.0 (0.2) | 119.8 (2.2) | 9.0 (0.3) |

Example 3

Ectopic Expression of OsMADS1 Overcomes Photoperiod Dependency of Long-Day and Short-Day Flowering Plants Transgenic plants that constitutively express a rice MADS-box gene, OsMADS1, flower earlier than untransformed controls, indicating that the OsMADS1 gene is involved in controlling flowering time.

Nicotiana sylvestris, a long-day flowering plant, and N. tabacum cv. Maryland Mammoth, a short-day flowering plant, were transformed with pGA1209, which contains a kanamycin selectable marker and a chimeric fusion between the CaMV 35S promoter and OsMADS1-coding region by the Agrobacterium-mediated co-cultivation method (An et al., Binary vectors, In Gelven and Schilperoort, eds., Plant Molecular Biology Manual A3:1–19, Kluwer Academic Publishers, Dordrecht, Belgium, 1988). Transgenic plants were regenerated on kanamycin-containing culture medium. Transgenic plants were selfed and kanamycin-resistant T1 offspring were used for the entire experiment. Plants were grown under either a short-day growth condition (10 hr light) or a long-day growth condition (16 hr light).

Total RNA was isolated from leaves of transgenic plants by the guanidium thiocyanate method (Sambrook et al., Molecular Cloning: A Laboratory Manual, Cold Spring Harbor Press, Cold Spring Harbor, N.Y., 1989). Twenty µg of total RNA was electrophoresed on a 1.3% agarose gel, blotted onto a nylon membrane, and hybridized with a $^{32}$P-labeled probe prepared by the random-priming method (Sambrook et al., Molecular Cloning: A Laboratory Manual, Cold Spring Harbor Press, Cold Spring Harbor, N.Y., 1989).

Transgenic N. sylvestris flowered earlier than untransformed controls under the permissive flowering (long-day) conditions. Plants were short and branched with clustered flowers compared to the controls. These phenotypes are similar to day-neutral transgenic tobacco plants expressing the OsMADS1 gene, In order to confirm whether the phenotypes were stably inherited, five independently transformed transgenic plants were chosen for further studies. T1 offspring were selected on a kanamycin-containing medium and the seedlings were grown under the long-day or short-day conditions. Under the long-day condition, the transgenic plants flowered 7–11 days earlier than the controls which flowered in 106 days after seed germination. The data are summarized in Table 3.

TABLE 3

Ectopic expression of OSMADS1 in Nicotiana sylvestris

| Transgenic Plant | Short Day Condition (10 h) | | Long Day Condition (16 h) | |
|---|---|---|---|---|
| | Days to Flowering | Height (cm) | Days to Flowering | Height (cm) |
| 1 | 102 | 62 | 98 | 68 |
| 2 | 85 | 35 | 95 | 45 |
| 3 | 146 | 65 | 99 | 72 |
| 4 | 84 | 36 | 96 | 46 |
| 5 | 97 | 52 | 97 | 52 |
| control | — | — | 106 | 85 |

The transgenic plants also showed short and branched phenotypes. When the transgenic plants were grown under the short-day (non-permissive) condition, they flowered within 85–146 days, whereas the untransformed control plants did not flower (Table 3). Transgenic line 2 and 4 flowered earlier under the short-day condition and the line 3 flowered under the long-day condition, while the line 1 and 5 flowered at approximately the same time.

In order to confirm whether the phenotypes observed resulted from the expression of the OsMADS1 gene, RNA blot analysis was performed. Since a constitutive promoter was used for expression of the gene, it was expected that the transcript was present in all the plant parts, since the 35S promoter-driven OsMADS1 transcript is almost equally expressed in both leaves and flowers. Total RNA was prepared from fully expanded leaves of five transgenic lines and the level of OsMADS1 transcript in each line was measured using the OsMADS1 cDNA probe.

All the transgenic plants expressed the OsMADS1 transcript. The amount of the transcript was in direct correlation with the degree of the phenotypes. Transgenic lines 2 and 4, which flowered earliest, expressed the highest level of the OsMADS1 mRNA, whereas line 3, which flowered latest among the five transgenic lines, expressed the lowest level of the OsMADS1 mRNA. Transgenic lines with intermediate phenotypes expressed intermediate levels of the transcript.

These results suggest that expression of the OsMADS1 gene caused a change in the timing of flowering in a long-day flowering plant N. sylvestris. Under permissive long-day conditions, transgenic plants flowered earlier than controls. Under non-permissive short-day conditions, expression of the transgene overcame the day-length requirement for flowering. The degree of the phenotype correlated with the level of expression of the transgene, especially under short-day conditions. Interestingly, transgenic plants expressing a high level of the OsMADS transcript flowered earlier under short-day conditions than under long-day conditions, the latter being permissive flowering conditions for untransformed N. sylvestris.

Expression of the OsMADS1 gene can also overcome the day-length requirement of a short-day flowering plant, N. tabacum cv. Maryland Mammoth. Transgenic plants were obtained that expressed the OsMADS1 chimeric molecule. As observed with the day-neutral or long-day plant, transformation of the OsMADS1 chimeric gene into the short-day plant resulted in early flowering and bushy phenotypes under a short-day (permissive) condition.

Three independently transformed lines were further studied. T1 offspring were selected on kanamycin-containing medium and grown under a short-day (permissive) or a long-day (non-permissive) conditions. Under permissive conditions, T1 transgenic lines flowered 16–21 days earlier than untransformed controls, which flowered in 119 days (Table 4). The height of the transgenic plants was less than one-half that of the control plants. Under non-permissive conditions, transgenic plants flowered in 202–206 days, whereas the control did not flower (Table 4).

RNA blot analysis showed that all three lines expressed the OsMADS1 transcript. Again, the degree of the phenotype correlated with the level of OsMADS1 transgene expression. Thus, expression of the OsMADS1 gene also overcame the day-length requirement of a short-day plant.

TABLE 4

Ectopic expression of OsMADS1 in Nicotiana tabacum cv. Maryland Mammoth

| Transgenic Plant | Short Day Condition (10 h) | | Long Day condition (16 h) | |
|---|---|---|---|---|
| | Days to Flowering | Height (cm) | Days to Flowering | Height (cm) |
| 1 | 98 | 61 | 202 | 102 |
| 2 | 103 | 65 | 206 | 105 |
| 3 | 98 | 63 | 203 | 104 |
| control | 119 | 143 | — | — |

Ectopic expression of OsMADS1 overcomes the day-length dependence of flowering. The effect was more evident when the gene was highly expressed. The fact that OsMADS1 overcomes the day-length dependence of both short-day and long-day plants indicates that a common gene product controls the timing of flowering in both short-day and long-day plants. It is likely that, under natural conditions, expression of the OsMADS1 gene is tightly controlled by environmental conditions and the flowering process is initiated by triggering OsMADS1 gene expression.

Example 4

Isolation and Analysis of a MADS-Box Gene from
Nicotiana tabacum, NtMADS3

A homolog of OsMADS1 was isolated from a *Nicotiana tabacum* cDNA library constructed using the λZapII vector (Stratagene, La Jolla, Calif.) and poly(A)+ mRNA isolated from tobacco flowers as described above. Using the OsMADS1 cDNA as a probe under moderately stringent hybridization conditions (60° C.) in an initial screen, several tobacco MADS-box genes were obtained.

In a secondary screen to identify a tobacco homolog of OsMADS1, the OsMADS1 cDNA was split into two parts between the MADS-box and K-box sequences and used to probe the tobacco MADS-box cDNAs. Only one of the cDNAs, NtMADS3, hybridized to both halves of the OsMADS1 sequence, i.e., to the half containing the MADS-box sequence and the half containing the OsMADS1 K-box sequence.

To further confirm the identity of NtMADS3 as a homolog of OsMADS1, all isolated tobacco MADS-box genes obtained in the primary screening of the tobacco flower library were placed under the control of the 35S promoter and transformed into *N. tabacum* as described above. Only transgenic *N. tabacum* expressing the NtMADS3 transgene exhibited early flowering and dwarf phenotypes.

The nucleotide sequence of the NtMADS3 cDNA was obtained and compared to OsMADS1. NtMADS3 is 945 bp long and contains an open reading frame of 242 amino acid residues (FIG. 2; SEQ ID NO:9). The deduced NtMADS3 polypeptide sequence (SEQ ID NO:9) showed 56% homology with that of OsMADS1 (SEQ ID NO:1), with 96.5% homology in the MADS-box and 77.3% homology in the K-box (FIG. 3).

All publications and published patent documents cited in this specification are incorporated herein by reference to the same extent as if each individual publication or patent application was specifically and individually indicated to be incorporated by reference.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 1141 base pairs
        ( B ) TYPE: nucleic acid
        ( C ) STRANDEDNESS: double stranded
        ( D ) TOPOLOGY: linear ( i x ) FEATURE:
        ( A ) NAME/KEY: MADS box
        ( B ) LOCATION: Residues 2-57 of deduced amino acid
            sequence of SEQ ID NO: 1:
        ( C ) IDENTIFICATION METHOD: Homology to MADS-box proteins
        FEATURE:
        ( A ) NAME/KEY: K-Box
        ( B ) LOCATION: Residues 90-143 of deduced amino acid
            sequence of SEQ ID NO: 1:
        ( C ) IDENTIFICATION METHOD: Homology to MADS-box proteins ( x i ) SEQUENCE DESCRIPTION: SEQ ID NO:1:

```
AAAACTAGCT  TGCAAAGGGG  ATAGAGTAGT  AGAGAGAGAG  AGAGAGGAGA  GGAGGAGGAA         60

GAAG                                                                          64

ATG  GGG  AGG  GGG  AAG  GTG  GAG  CTG  AAG  CGG  ATC  GAG  AAC  AAG  ATC  AGC   112
Met  Gly  Arg  Gly  Lys  Val  Glu  Leu  Lys  Arg  Ile  Glu  Asn  Lys  Ile  Ser
 1              5                        10                       15

CGG  CAG  GTG  ACG  TTC  GCC  AAG  CGC  AGG  AAC  GGC  CTG  CTC  AAG  AAG  GCC   160
Arg  Gln  Val  Thr  Phe  Ala  Lys  Arg  Arg  Asn  Gly  Leu  Leu  Lys  Lys  Ala
              20                        25                       30

TAC  GAG  CTC  TCC  CTC  CTC  TGC  GAC  GCC  GAG  GTC  GCC  CTC  ATC  ATC  TTC   208
```

```
                Tyr  Glu  Leu  Ser  Leu  Leu  Cys  Asp  Ala  Glu  Val  Ala  Leu  Ile  Ile  Phe
                          35                       40                  45

TCC  GGC  CGC  GGC  CGC  CTC  TTC  GAG  TTC  TCC  AGC  TCA  TCA  TGC  ATG  TAC                    256
Ser  Gly  Arg  Gly  Arg  Leu  Phe  Glu  Phe  Ser  Ser  Ser  Ser  Cys  Met  Tyr
     50                       55                       60

AAA  ACC  TTG  GAG  AGG  TAC  CGC  AGC  TGC  AAC  TAC  AAC  TCA  CAG  GAT  GCA                    304
Lys  Thr  Leu  Glu  Arg  Tyr  Arg  Ser  Cys  Asn  Tyr  Asn  Ser  Gln  Asp  Ala
65                       70                       75                       80

GCA  GCT  CCA  GAA  AAC  GAA  ATT  AAT  TAC  CAA  GAA  TAC  CTG  AAG  CTG  AAA                    352
Ala  Ala  Pro  Glu  Asn  Glu  Ile  Asn  Tyr  Gln  Glu  Tyr  Leu  Lys  Leu  Lys
                    85                       90                       95

ACA  AGA  GTT  GAA  TTT  CTT  CAA  ACC  ACA  CAG  AGA  AAT  ATT  CTT  GGT  GAG                    400
Thr  Arg  Val  Glu  Phe  Leu  Gln  Thr  Thr  Gln  Arg  Asn  Ile  Leu  Gly  Glu
               100                      105                      110

GAT  TTG  GGC  CCA  CTA  AGC  ATG  AAG  GAG  CTG  GAG  CAG  CTT  GAG  AAC  CAG                    448
Leu  Ser  Met  Asp  Leu  Gly  Pro  Lys  Glu  Leu  Glu  Gln  Leu  Glu  Asn  Gln
          115                      120                      125

ATA  GAA  GTA  TCC  CTC  AAA  CAA  ATC  AGG  TCA  AGA  AAG  AAC  CAA  GCA  CTG                    496
Ile  Glu  Val  Ser  Leu  Lys  Gln  Ile  Arg  Ser  Arg  Lys  Asn  Gln  Ala  Leu
     130                      135                      140

CTT  GAT  CAG  CTG  TTT  GAT  CTG  AAG  AGC  AAG  GAG  CAA  CAG  CTG  CAA  GAT                    544
Leu  Asp  Gln  Leu  Phe  Asp  Leu  Lys  Ser  Lys  Glu  Gln  Gln  Leu  Gln  Asp
145                      150                      155                      160

CTC  AAC  AAA  GAC  TTG  AGG  AAA  AAG  TTA  CAG  GAA  ACC  AGT  GCA  GAG  AAT                    592
Leu  Asn  Lys  Asp  Leu  Arg  Lys  Lys  Leu  Gln  Glu  Thr  Ser  Ala  Glu  Asn
                    165                      170                      175

GTG  CTC  CAT  ATG  TCC  TGG  CAA  GAT  GGT  GGT  GGG  CAC  AGC  GGT  TCT  AGC                    640
Val  Leu  His  Met  Ser  Trp  Gln  Asp  Gly  Gly  Gly  His  Ser  Gly  Ser  Ser
               180                      185                      190

ACT  GTT  CTT  GCT  GAT  CAG  CCT  CAT  CAC  CAT  CAG  GGT  CTT  CTC  CAC  CCT                    688
Thr  Val  Leu  Ala  Asp  Gln  Pro  His  His  His  Gln  Gly  Leu  Leu  His  Pro
          195                      200                      205

CAC  CCA  GAT  CAG  GGT  GAC  CAT  TCC  CTG  CAG  ATT  GGG  TAT  CAT  CAC  CCT                    736
His  Pro  Asp  Gln  Gly  Asp  His  Ser  Leu  Gln  Ile  Gly  Tyr  His  His  Pro
     210                      215                      220

CAT  GCT  CAC  CAT  CAC  CAG  GCC  TAC  ATG  GAC  CAT  CTG  AGC  AAT  GAA  GCA                    784
His  Ala  His  His  His  Gln  Ala  Tyr  Met  Asp  His  Leu  Ser  Asn  Glu  Ala
225                      230                      235                      240

GCA  GAC  ATG  GTT  GCT  CAT  CAC  CCC  AAT  GAA  CAC  ATC  CCA  TCC  GGC  TGG                    832
Ala  Asp  Met  Val  Ala  His  His  Pro  Asn  Glu  His  Ile  Pro  Ser  Gly  Trp
                    245                      250                      255

ATA  TGA                                                                                           838
Ile

TGTGTGTGTT  CAGTTCAGGC  TTCAGGCTTC  AGAGAAGCCA  ATGCAAACAG  TGTCCTGTAA                              898

TCCAGTAATT  ACAGGGCATA  TGTAATGTAA  TGTAATGTAA  TCCCTGATCT  ATATTTGCT                               958

AAGTACGTGC  GTGCTCTCTT  ACGACCTTCT  CCCCCAAACA  GTTAATCAGG  GGAATAATAA                             1018

TTTCGTTTGA  TGCACGTACT  GTATGTCTGT  ATCTGTCACT  GTATCGTAGG  ACCGTCCATG                             1078

TATAACAATT  TCCGTTTTGG  ATGTGGTAAC  AATTAATTGG  CACTTAAATT  TATATTTGTG                             1138

ATG                                                                                               1141
```

( 2 ) INFORMATION FOR SEQ ID NO: 2:

( i ) SEQUENCE CHARACTERISTICS:
        ( A ) LENGTH: 56 amino acids
        ( B ) TYPE: amino acid (deduced)
        ( D ) TOPOLOGY: linear ( i x ) FEATURE:
        ( A ) NAME/KEY: Homology with AP1, SQUA, AG, PLE, AP3, DEFA
            ( B ) LOCATION: Amino acids 1- 56
            ( C ) IDENTIFICATION METHOD: Amino acid sequence homology
            ( D ) OTHER INFORMATION: MADS-box region of SEQ ID NO:1,
                    amino acids 2-57

( x i ) SEQUENCE DESCRIPTION: SEQ ID NO:2:

Gly Arg Gly Lys Val Glu Leu Lys Arg Ile Glu Asn Lys Ile Ser Arg
                  5                   10                  15
Gln Val Thr Phe Ala Lys Arg Arg Asn Gly Leu Leu Lys Lys Ala Tyr
                 20                  25                  30
Glu Leu Ser Leu Leu Cys Asp Ala Glu Val Ala Leu Ile Ile Phe Ser
             35                  40                  45
Gly Arg Gly Arg Leu Phe Glu Phe
         50                  55

( 2 ) INFORMATION FOR SEQ ID NO: 3:

( i ) SEQUENCE CHARACTERISTICS:
            ( A ) LENGTH: 56 amino acids
            ( B ) TYPE: amino acid (deduced)
            ( D ) TOPOLOGY: linear ( i x ) FEATURE:
            ( A ) NAME/KEY: Homology with SEQ ID NO:2
            ( B ) LOCATION: Amino acids 1- 56
            ( C ) IDENTIFICATION METHOD: Amino acid sequence homology
            ( D ) OTHER INFORMATION: MADS-box region of AP1

( x i ) SEQUENCE DESCRIPTION: SEQ ID NO:3:

Gly Arg Gly Arg Val Gln Leu Lys Arg Ile Glu Asn Lys Ile Asn Arg
                  5                   10                  15
Gln Val Thr Phe Ser Lys Arg Arg Ala Gly Leu Leu Lys Lys Ala His
                 20                  25                  30
Glu Ile Ser Val Leu Cys Asp Ala Glu Val Ala Leu Val Val Phe Ser
             35                  40                  45
His Lys Gly Lys Leu Phe Glu Tyr
         50                  55

( 2 ) INFORMATION FOR SEQ ID NO: 4:

( i ) SEQUENCE CHARACTERISTICS:
            ( A ) LENGTH: 56 amino acids
            ( B ) TYPE: amino acid
            ( D ) TOPOLOGY: linear ( i x ) FEATURE:
            ( A ) NAME/KEY: Homology with SEQ ID NO:2
            ( B ) LOCATION: Amino acids 1- 56
            ( C ) IDENTIFICATION METHOD: Amino acid sequence homology
            ( D ) OTHER INFORMATION: MADS-box region of SQUA ( x i ) SEQUENCE DESCRIPTION: SEQ ID NO:4:

Gly Arg Gly Lys Val Gln Leu Lys Arg Ile Glu Asn Lys Ile Asn Arg
                  5                   10                  15
Gln Val Thr Phe Ser Lys Arg Arg Gly Gly Leu Leu Lys Lys Ala His
                 20                  25                  30
Glu Leu Ser Val Leu Cys Asp Ala Glu Val Ala Leu Ile Val Phe Ser
             35                  40                  45
Asn Lys Gly Lys Leu Phe Glu Tyr
         50                  55

( 2 ) INFORMATION FOR SEQ ID NO: 5:

( i ) SEQUENCE CHARACTERISTICS:

(A) LENGTH: 56 amino acids
(B) TYPE: amino acid
(D) TOPOLOGY: linear (ix) FEATURE:
(A) NAME/KEY: Homology with SEQ ID NO:2
(B) LOCATION: Amino acids 1- 56
(C) IDENTIFICATION METHOD: Amino acid sequence homology
(D) OTHER INFORMATION: MADS-box region of AG (xi) SEQUENCE DESCRIPTION: SEQ ID NO:5:

Gly Arg Gly Lys Ile Glu Ile Lys Arg Ile Glu Asn Thr Thr Asn Arg
                 5                  10                 15
Gln Val Thr Phe Cys Lys Arg Arg Asn Gly Leu Leu Lys Lys Ala Tyr
             20                 25                 30
Glu Leu Ser Val Leu Cys Asp Ala Glu Val Ala Leu Ile Val Phe Ser
         35                 40                 45
Ser Arg Gly Arg Leu Tyr Glu Tyr
     50                  55

(2) INFORMATION FOR SEQ ID NO: 6:

(i) SEQUENCE CHARACTERISTICS:
(A) LENGTH: 56 amino acid residues
(B) TYPE: amino acid
(D) TOPOLOGY: linear (ix) FEATURE:
(A) NAME/KEY: Homology with SEQ ID NO:2
(B) LOCATION: Amino acids 1- 56
(C) IDENTIFICATION METHOD: Amino acid sequence homology
(D) OTHER INFORMATION: MADS-box region of PLE (xi) SEQUENCE DESCRIPTION: SEQ ID NO:6:

Gly Arg Gly Lys Ile Glu Ile Lys Arg Ile Glu Asn Ile Thr Asn Arg
                 5                  10                 15
Gln Val Thr Phe Cys Lys Arg Arg Asn Gly Leu Leu Lys Lys Ala Tyr
             20                 25                 30
Glu Leu Ser Val Leu Cys Asp Ala Glu Val Ala Leu Val Val Phe Ser
         35                 40                 45
Ser Arg Gly Arg Leu Tyr Glu Tyr
     50                  55

(2) INFORMATION FOR SEQ ID NO: 7:

(i) SEQUENCE CHARACTERISTICS:
(A) LENGTH: 56 amino acids
(B) TYPE: amino acid
(D) TOPOLOGY: linear (ix) FEATURE:
(A) NAME/KEY: Homology with SEQ ID NO:2
(B) LOCATION: Amino acids 1- 56
(C) IDENTIFICATION METHOD: Amino acid sequence homology
(D) OTHER INFORMATION: MADS-box region of AP3

(xi) SEQUENCE DESCRIPTION: SEQ ID NO:7:

Gly Gly Gly Arg Val Gln Leu Lys Arg Ile Glu Asn Gln Thr Asn Arg
                 5                  10                 15
Gln Val Thr Tyr Ser Lys Arg Arg Asn Gly Leu Phe Lys Lys Ala His
             20                 25                 30
Glu Leu Thr Val Leu Cys Asp Ala Arg Val Ser Ile Ile Met Phe Ser
         35                 40                 45
Ser Ser Asn Lys Leu His Glu Tyr
     50                  55

( 2 ) INFORMATION FOR SEQ ID NO: 8:

( i ) SEQUENCE CHARACTERISTICS:
        ( A ) LENGTH: 56 amino acid residues
        ( B ) TYPE: amino acid (deduced)
        ( D ) TOPOLOGY: linear ( i x ) FEATURE:
        ( A ) NAME/KEY: Homology with SEQ ID NO:2
        ( B ) LOCATION: Amino acids 1- 56
        ( C ) IDENTIFICATION METHOD: Amino acid sequence homology
        ( D ) OTHER INFORMATION: MADS-box region of DEFA ( x i ) SEQUENCE DESCRIPTION: SEQ ID NO:8:

```
Ala  Arg  Gly  Lys  Ile  Gln  Ile  Lys  Arg  Ile  Glu  Asn  Gln  Thr  Asn  Arg
               5                        10                       15

Gln  Val  Thr  Tyr  Ser  Lys  Arg  Arg  Asn  Gly  Leu  Phe  Lys  Lys  Ala  His
               20                       25                       30

Glu  Leu  Ser  Val  Leu  Cys  Asp  Ala  Lys  Val  Ser  Ile  Ile  Met  Ile  Ser
               35                       40                       45

Ser  Thr  Gln  Lys  Leu  His  Glu  Tyr
               50                       55
```

( 2 ) INFORMATION FOR SEQ ID NO: 9:

( i ) SEQUENCE CHARACTERISTICS:
        ( A ) LENGTH: 945 base pairs
        ( B ) TYPE: nucleic acid
        ( C ) STRANDEDNESS: double stranded
        ( D ) TOPOLOGY: linear ( x i ) SEQUENCE DESCRIPTION: SEQ ID NO:9:

```
CCGGCCGCTGAAAAA                                                                                   15

ATG  GGA  AGG  GGT  AGG  GTT  GAG  CTT  AAG  AGA  ATA  GAG  AAC  AAG  ATC  AAC    63
Met  Gly  Arg  Gly  Arg  Val  Glu  Leu  Lys  Arg  Ile  Glu  Asn  Lys  Ile  Asn
1                   5                        10                       15

AGG  CAA  GTG  ACC  TTC  GCT  AAG  AGA  AGA  AAT  GGA  CTT  TTG  AAA  AAA  GCT   111
Arg  Gln  Val  Thr  Phe  Ala  Lys  Arg  Arg  Asn  Gly  Leu  Leu  Lys  Lys  Ala
                    20                       25                       30

TAT  GAG  CTT  TCT  GTT  CTT  TGT  GAT  GCT  GAG  GTT  GCT  CTC  ATC  ATC  TTC   159
Tyr  Glu  Leu  Ser  Val  Leu  Cys  Asp  Ala  Glu  Val  Ala  Leu  Ile  Ile  Phe
               35                       40                       45

TCC  AAT  AGG  GGA  AAA  CTG  TAC  GAG  TTC  TGC  AGT  AGC  TCT  AGC  ATG  CTC   207
Ser  Asn  Arg  Gly  Lys  Leu  Tyr  Glu  Gly  Cys  Ser  Ser  Ser  Ser  Met  Leu
          50                       55                       60

AAG  ACA  TTA  GAG  AGG  TAC  CAG  AAG  TGC  AAC  TAC  GGA  GCA  CCA  GAG  ACC   255
Lys  Thr  Leu  Glu  Arg  Tyr  Gln  Lys  Cys  Asn  Tyr  Gly  Ala  Pro  Glu  Thr
65                       70                       75                       80

AAT  ATA  TCC  ACA  CGA  GAA  GCA  CTG  GAA  ATA  AGT  AGC  CAA  CAA  GAA  TAC   303
Asn  Ile  Ser  Thr  Arg  Glu  Ala  Leu  Glu  Ile  Ser  Ser  Gln  Gln  Glu  Tyr
                    85                       90                       95

TTG  AAG  CTT  AAA  GCA  CGT  TAC  GAA  GCA  TTA  CAG  CGA  TCA  CAG  AGA  AAT   351
Leu  Lys  Leu  Lys  Ala  Arg  Tyr  Glu  Ala  Leu  Gln  Arg  Ser  Gln  Arg  Asn
               100                      105                      110

CTT  CTT  GGT  GAA  GAT  CTT  GGC  CCT  TTG  AAT  AGC  AAG  GAA  CTT  GAA  TCA   399
Leu  Leu  Gly  Glu  Asp  Leu  Gly  Pro  Leu  Asn  Ser  Lys  Glu  Leu  Glu  Ser
          115                      120                      125

CTT  GAG  AGG  CAG  CTT  GAT  ATG  TCA  CTG  AAA  CAG  ATT  CGA  TCA  ACT  CGG   447
Leu  Glu  Arg  Gln  Leu  Asp  Met  Ser  Leu  Lys  Gln  Ile  Arg  Ser  Thr  Arg
          130                      135                      140

ACT  CAG  TTA  ATG  TTG  GAT  CAA  CTT  ACA  GAT  CTT  CAG  AGA  AAG  GAA  CAT   495
Thr  Gln  Leu  Met  Leu  Asp  Gln  Leu  Thr  Asp  Leu  Gln  Arg  Lys  Glu  His
145                      150                      155                      160
```

-continued

| | | | | | | | | | | | | | | | | |
|---|---|---|---|---|---|---|---|---|---|---|---|---|---|---|---|---|
| GCA | TTA | AAC | GAA | GCA | AAC | AGA | ACC | TTG | AAA | CAA | AGG | TTG | ATG | GAA | GGA | 543 |
| Ala | Leu | Asn | Glu | Ala | Asn | Arg | Thr | Leu | Lys | Gln | Arg | Leu | Met | Glu | Gly | |
| | | | | 165 | | | | | 170 | | | | | 175 | | |
| AGC | CAA | CTA | AAT | CTG | CAG | TGG | CAA | CAA | AAT | GCA | CAA | GAT | ATG | GGC | TAC | 591 |
| Ser | Gln | Leu | Asn | Leu | Gln | Trp | Gln | Gln | Asn | Ala | Gln | Asp | Met | Gly | Tyr | |
| | | | 180 | | | | | 185 | | | | | 190 | | | |
| GGC | CGG | CAA | ACA | ACT | CAA | ACT | CAG | GGC | GAT | GGC | TTT | TTT | CAT | CCT | TTG | 639 |
| Gly | Arg | Gln | Thr | Thr | Gln | Thr | Gln | Gly | Asp | Gly | Phe | Phe | His | Pro | Leu | |
| | | 195 | | | | | 200 | | | | | 205 | | | | |
| GAA | TGT | GAA | CCC | ACT | TTG | CAA | ATT | GGG | TAT | CAG | AAT | GAT | CCA | ATA | ACA | 687 |
| Glu | Cys | Glu | Pro | Thr | Leu | Gln | Ile | Gly | Tyr | Gln | Asn | Asp | Pro | Ile | Thr | |
| | 210 | | | | | 215 | | | | | 220 | | | | | |
| GTA | GGA | GGA | GCA | GGG | CCC | AGT | GTG | AAT | AAC | TAC | ATG | GCT | GGC | TGG | TTG | 735 |
| Val | Gly | Gly | Ala | Gly | Pro | Ser | Val | Asn | Asn | Tyr | Met | Ala | Gly | Trp | Leu | |
| 225 | | | | | 230 | | | | | 235 | | | | | 240 | |
| CCT | TGA | | | | | | | | | | | | | | | 741 |
| Pro | | | | | | | | | | | | | | | | |

| | | | | |
|---|---|---|---|---|
| AATTAAGCTC | ATTTCCGATA | AGATTGATTA | TATAAACATA | TGCTCAATGT | TTTTCCTATC | 801 |
| ATAAACACTC | TCCTAATTTG | TGTTATATGT | TGTTTGCCGA | ATTCTGGACT | AATTTGGGAT | 861 |
| CCATAAGACA | GACCCGTTAT | TGTTACTTAA | TCATAAACTA | GATTTCCCTG | AGTGACTAAT | 921 |
| CACTAAAGCT | TATTACTTTC | CTCC | | | | 945 |

What is claimed is:

1. An isolated nucleic acid comprising a sequence selected from the group consisting of:
   (a) an allele of OSMADS1; and
   (b) a sequence of at least 100 consecutive nucleotides having at least 70% nucleotide sequence similarity with SEQ ID NO:1, not including MADS-box and K-box regions thereof, said sequence, when expressed in a transgenic plant, producing at least one phenotype in the transgenic plant selected from the group consisting of: (i) altered daylength requirement for flowering; (ii) greater synchronization of flowering; and (iii) a relaxed vernalization requirement.

2. The nucleic acid of claim 1 comprising a sequence of at least 100 consecutive nucleotides having at least 70% nucleotide sequence similarity with SEQ ID NO:1, not including MADS-box and K-box regions of SEQ ID NO:1, said sequence, when expressed in a tranogenic plant, producing at least one phenotype in the transgenic plant selected from the group consisting of: (i) altered daylength requirement for flowering; (ii) greater synchronization of flowering; and (iii) a relaxed vernalization requirement.

3. The nucleic acid of claim 2 wherein the sequence comprises only silent or conservative substitutions to SEQ ID NO:1 or SEQ ID NO:9.

4. A vector comprising the nucleic acid of claim 1.

5. A host cell comprising the nucleic acid of claim 1.

6. A transgenic plant comprising the nucleic acid of claim 1.

7. A method of using the host cell of claim 5, the method comprising the steps of:
   providing the host cell; and
   culturing the host cell under conditions suitable for expression of the sequence to produce a polypeptide encoded by the nucleic acid.

8. A method of producing a polypeptide, the method comprising the steps of:
   providing the host cell of claim 5; and
   culturing the host cell under conditions suitable for expression of the sequence to produce a polypeptide encoded by the nucleic acid.

9. A method of using a nucleic acid of claim 1 comprising the steps of:
   introducing the nucleic acid of claim 1 into a plant cell, thereby producing a transformed plant cell; and
   growing a plant having said at least one phenotype from the transformed plant cell.

10. The nucleic acid of claim 1 wherein the sequence is an allele of the OsMADS1 gene.

11. A method of producing a plant having at least one phenotype compared to a nontransgenic control plant, the phenotype being selected from the group consisting of (i) altered daylength requirement for flowering, (ii) greater synchronization of flowering, and (iii) relaxed vernalization requirement, the method comprising the steps of:
   (a) introducing into a cell of the plant a nucleic acid of claim 1, thereby producing a transformed cell;
   (b) growing a plant having said at least one phenotype from the transformed cell.

12. A transgenic plant of a long-day or short-day species having a substantially relaxed daylength requirement for flowering compared to a nontransgenic control plant, the transgenic plant comprising a recombinant nucleic acid that comprises a sequence of at least 100 consecutive nucleotides having at least 70% nucleotide sequence similarity with SEQ ID NO:1, not including MADS-1 box and K-box regions of SEQ ID NO:1, wherein said relaxed daylength requirement results from expression of the sequence.

13. The plant of claim 12 having a completely relaxed daylength requirement for flowering.

14. A method of producing multiple crops of flowers or fruits in a year from the plant of claim 12, the method comprising the steps of:
   (a) planting a reproductive unit of the plant;
   (b) growing the planted reproductive unit under natural light conditions;

(c) harvesting flowers or fruits of the plant; and (d) repeating steps (a) through (c) at least once in the year.

15. The nucleic acid of claim 1 wherein the sequence comprises the polypeptide-coding region of NtMADS3.

16. The nucleic acid of claim 15 comprising SEQ ID NO:9.

17. A vector comprising the nucleic acid of claim 15.

18. A host cell comprising the nucleic acid of claim 15.

19. A transgenic plant comprising the nucleic acid of claim 15.

20. A method of using a nucleic acid of claim 15 comprising the steps of:

introducing the nucleic acid of claim 15 into a plant cell, thereby producing a transformed plant cell; and growing a plant having an altered phenotype from the transformed plant cell.

21. The nucleic acid of claim 2 comprising a sequence having at least 80% nucleotide sequence similarity with SEQ ID NO:1, not including MADS-box and K-box regions of SEQ ID NO:1.

22. The nucleic acid of claim 2 comprising a sequence having at least 90% nucleotide sequence similarity with SEQ ID NO:1, not including MADS-box and K-box regions of SEQ ID NO:1.

23. A vector comprising the nucleic acid of claim 2.

24. A host cell comprising the nucleic acid of claim 2.

25. A transgenic plant comprising the nucleic acid of claim 2.

26. A method of using a nucleic acid of claim 2 comprising the steps of:

introducing the nucleic acid of claim 2 into a plant cell, thereby producing a transformed plant cell; and growing a plant having said at least one phenotype from the transformed plant cell.

27. An isolated nucleic acid comprising a sequence selected from the group consisting of:

(a) a NtMADS3 polypeptide-coding region;

(b) a NtMADS3 MADS-box sequence; and (c) a NtMADS3 K-box sequence.

28. The nucleic acid of claim 27 comprising a sequence selected from the group consisting of:

(a) a polypeptide-coding region of SEQ ID NO:9;

(b) a MADS-box sequence of SEQ ID NO:9; and (c) a K-box sequence of SEQ ID NO:9.

29. The nucleic acid of claim 28 comprising SEQ ID NO:9.

* * * * *

UNITED STATES PATENT AND TRADEMARK OFFICE
CERTIFICATE OF CORRECTION

PATENT NO. : 5,861,542
DATED : January 19, 1999
INVENTOR(S) : Gynheung An

It is certified that error appears in the above-identified patent and that said Letters Patent is hereby corrected as shown below:

Column 7, lines 13 and 14, "Oriza sativa" should be --*Oryza sativa*--.

Column 7, line 14, "biologically activities" should be --biological activities--.

Column 11, line 36, "gln, his" should be --gln; his--.

Column 11, line 43, "leu, val" should be --leu; val--.

Column 12, line 30, the end parenthesis ")" should be deleted.

Column 12, line 33, "substitutions" should be --insertions--.

Column 15, line 47, "1933" should be --1993--.

Column 17, line 6, "Juijser" should be --Huijser--.

Column 19, line 29, the comma "," at the end of the line should be a period --.--.

UNITED STATES PATENT AND TRADEMARK OFFICE
CERTIFICATE OF CORRECTION

PATENT NO. : 5,861,542
DATED : January 19, 1999
INVENTOR(S) : Gynheung An

It is certified that error appears in the above-identified patent and that said Letters Patent is hereby corrected as shown below:

In the Claims:

Column 31, line 33, claim 1, "OSMADS1" should be --OsMADS1--.

Signed and Sealed this

Twenty-eighth Day of March, 2000

Attest:

Q. TODD DICKINSON

*Attesting Officer*    *Commissioner of Patents and Trademarks*